US011713493B2

(12) United States Patent
Park et al.

(10) Patent No.: US 11,713,493 B2
(45) Date of Patent: *Aug. 1, 2023

(54) COMPOSITIONS AND METHODS OF USE THEREOF FOR RARE EARTH ELEMENT SEPARATION

(71) Applicant: Lawrence Livermore National Security, LLC, Livermore, CA (US)

(72) Inventors: Dan Mcfarland Park, Dublin, CA (US); Aaron William Brewer, Livermore, CA (US); Yongqin Jiao, Pleasanton, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/289,382

(22) Filed: Feb. 28, 2019

(65) Prior Publication Data

US 2020/0277684 A1 Sep. 3, 2020

(51) Int. Cl.
*C22B 3/18* (2006.01)
*C22B 59/00* (2006.01)
*C12P 3/00* (2006.01)
*C12N 1/20* (2006.01)

(52) U.S. Cl.
CPC .......... *C22B 3/18* (2013.01); *C12P 3/00* (2013.01); *C22B 59/00* (2013.01); *C12N 1/20* (2013.01)

(58) Field of Classification Search
CPC ....................................................... C22B 3/18
See application file for complete search history.

(56) References Cited

U.S. PATENT DOCUMENTS

| | | | |
|---|---|---|---|
| 4,683,196 A | 7/1987 | Mclaughlin | |
| 5,512,435 A | 4/1996 | Renschler et al. | |
| 10,196,708 B2 * | 2/2019 | Jiao | C07K 14/4728 |
| 2003/0228622 A1 | 12/2003 | Imperiali et al. | |
| 2018/0195147 A1 * | 7/2018 | Jiao | C12P 3/00 |
| 2020/0048732 A1 * | 2/2020 | Barker | C02F 1/001 |

FOREIGN PATENT DOCUMENTS

| WO | 2015111407 A1 | 7/2015 | |
|---|---|---|---|
| WO | WO-2017136561 A1 * | 8/2017 | C12N 11/10 |

OTHER PUBLICATIONS

Park et al., Recovery of Rare Earth Elements from Low-Grade Feedstock Leachates Using Engineered Bacteria, Environ. Sci. Technol. 2017, 51, 13471-13480 (Year: 2017).*
Cotton, S., "Lanthanide and Actinide Chemistry", John Wiley & Sons Ltd, 2006, 267 pages.
Cox, S., J., et al., "Characterizing Heterogeneous Bacterial Surface Functional Groups Using Discrete Affinity Spectra for Proton Binding" Department of Geology, Environmental Science & Technology, vol. 33, No. 24, 1999, 8 pages.
Dent, C., P., "Rare earth elements and permanent magnets (invited)", Journal of Applied Physics, Mar. 2012, 7 pages.
Gadd, M., G., "Biosorption: critical review of scientific rationale, environmental importance and significance for pollution treatment", Society of Chemical Industry, Jul. 2008, 16 pages.
Gupta, K., C., "Extractive Metallurgy of Rare Earths", CRC Press, 2005, 484 pages.
Hansel, M., C., "Coupled Photochemical and Enzymatic Mn(II) Oxidation Pathways of a Planktonic Roseobacter-Like Bacterium", American Society for Microbiology, Feb. 2006, 7 pages.
Hosomomi, Y., et al., "Biosorption of Rare Earth Elements by *E. coli*", Journal of Chemical Engineering of Japan, Jun. 2013, 22 pages.
Humphries, M., "Rare Earth Elements: The Global Supply Chain", Congressional Research Services, Dec. 2013, 31 pages.
Kazy, K. S., et al., "Lanthanum biosorption by a Pseudomonas sp.: equilibrium studies and chemical characterization", Society for Industrial Microbiology, Apr. 2006, 11 pages.
Kelly, D., S., et al., "X-ray absorption fine structure determination of pH-dependent U-bacterial cell wall interactions", Geochimica et Cosmochimica Acta, vol. 66, No. 22, Apr. 2002, 17 pages.
Kotrba, P., "Microbial Biosorption of Metals", Springer Science and Business Media B.V., 2011, 334 pages.
Markai, S., "Study of the interaction between europium (III) and Bacillus subtilis: fixation sites, biosorption modeling and reversibility", Journal of Colloid and Interface Science 262 (2003) 351-361.
Ngwenya, T., B., et al., "Macroscopic and spectroscopic analysis of lanthanide adsorption to bacterial cells", Geochimica et Cosmochimica Acta 73 (2009) 3134-3147.
Park, M., D., "Recovery of Rare Earth Elements from Low-Grade Feedstock Leachates Using Engineered Bacteria", Environmental Science & Technology, 2017, 51, 10 pages.
Takahashi, Y., "EXAFS study on the cause of enrichment of heavy REEs on bacterial cell surfaces", Geochimica et Cosmochimica Acta 74 (2010) 5443-5462.
Takahashi, Y., et al. "Adsorption of rare earth elements onto bacterial cell walls and its implication for REE sorption onto natural microbial mats", Chemical Geology 219 (2005) 53-67.
Texier, A., et al., "Characterization of Lanthanide Ions Binding Sites in the Cell Wall of Pseudomonas aeruginosa", Environ. Sci. Technol. 2000, 34, 610-615.
U.S. Department of Energy, "Critical Materials Strategy", Dec. 2011, 196 pages.
Vogel, C., "Metal accumulation by heterotrophic marine bacterioplankton", Limnol. Oceanogr., 55(2), 2010, 519-528.
Abate, A. R. et al., "High-Order Multiple Emulsions Formed in Poly(dimethylsiloxane) Microfluidics", Small Journal, 5(18):2030-2032, Sep. 2009, Sep. 2009, 2030-2032.
Acerce, Muharrem et al., "Metallic 1T phase MoS2 nanosheets as supercapacitor electrode materials", Nature Nanotechnology, 10(4):313-318, Mar. 2015, Mar. 2015, 313-318.
Allen, Karen N. et al., "Lanthanide-tagged proteins—an illuminating partnership", Current Opinion in Chemical Biology, 14(2):247-254, Apr. 2010, Apr. 2010, 247-254.

(Continued)

*Primary Examiner* — Antonio Galisteo Gonzalez
(74) *Attorney, Agent, or Firm* — Perkins Coie LLP

(57) ABSTRACT

This disclosure provides engineered microbes coding at least one rare earth element (REE) binding ligand for the preferential separation of REEs, as well as methods of use thereof.

30 Claims, 14 Drawing Sheets

(56) References Cited

OTHER PUBLICATIONS

Anastopoulos, Ioannis, et al., "Adsorption of rare earth metals: A review of recent literature", Journal of Molecular Liquids 2016, 221, 954-962, 2016, 221,954-962.

Bayer, M. E. et al., "Lanthanide Accumulation in the Periplasmic Space of Escherichia coli B", Journal of Bacteriology, 173(1):141-149, Jan. 1991, Jan. 1991, 141-149.

Binnemans, Koen et al., "Recycling of rare earths: a critical review", Journal of Cleaner Production, 51:1-22, Jul. 2013, Jul. 2013, 1-22.

Bonificio, William D. et al., "Rare-Earth Separation Using Bacteria Environ", Sci Technol Lett 2016, 3 180-184, 2016, 180-184.

Bünzli, Jean-Claude G., "Benefiting from the Unique Properties of Lanthanide Ions", Accounts of Chemical Research, 39(1):53-61, Jan. 2006, Jan. 2006, 53-61.

Cheng, Yung-Chi et al., "Relationship between the inhibition constant (K1) and the concentration of inhibitor which causes 50 percent inhibition (I50) of an enzymatic reaction", Biochemical Pharmacology, 22(23):3099-3108, Dec. 1973, Dec. 1973, 3099-3108.

Chi, R et al., "A solution chemistry approach to the study of rare earth element precipitation by oxalic acid", Metallurgical and Materials Transactions B, 30(2):189-195, Apr. 1999, Apr. 1999, 189-195.

Daumann, Lena J. et al., "Siderophore inspired tetra- and octadentate antenna ligands for luminescent Eu(III) and Tb(III) complexes", Journal of Inorganic Biochemistry, 162:263-273, Sep. 2016, Sep. 2016, 263-273.

Eggert, Roderick, "Rare Earths: Market disruption, innovation, and global supply chains", Annu. Rev. Environ. Resour. 2016, 41, 199-222, Aug. 9, 2016, 199-222.

Entcheva-Dimitrov, Plamen et al., "Dynamics and Control of Biofilms of the Oligotrophic Bacterium Caulobacter rescentus", Journal of Bacteriology, 186(24):8254-8266, Dec. 2004, Dec. 2004, 8254-8266.

Firsching, F. H. et al., "Solubility Products of the Trivalent Rare-Earth Phosphates", Journal of Chemical & Engineering Data, 36(1):93-95, Jan. 1991, Jan. 1991, 93-95.

Franz, Katherine J. et al., "Lanthanide-Binding Tags as Versatile Protein Coexpression Probes", Chembiochem, 4(4):265-271, Mar. 26, 2003, Mar. 26, 2003, 265-271.

Fujita, Yoshiko et al., "Effects of Simulated Rare Earth Recycling Wastewaters on Biological Nitrification", Environmental Science & Technology, 49(16):9460-9468, Jul. 2015, Jul. 2015, 9460-9468.

Gadd, Geoffrey M., "Metals, minerals and microbes: geomicrobiology and bioremediation", Microbiology, 156(3):609-643, Mar. 2010, Mar. 2010, 609-643.

Gomes, Helena I. et al., "Alkaline residues and the environment: a review of impacts, management practices and opportunities", Journal of Cleaner Production, 112(4):3571-3582, Jan. 2016, Jan. 2016, 3571-3582.

Goyne, Keith W. et al., "Rare earth element release from phosphate minerals in the presence of organic acids", Chemical Geology, 278(1-2):1-14, Nov. 2010, Nov. 2010, 1-14.

Hennebel, Tom et al., "Biotechnologies for critical raw material recovery from primary and secondary sources: R&D priorities and future perspectives", New Biotechnology, 32(1):121-127, Jan. 2015, Jan. 2015, 121-127.

Herrera, Carmen M. et al., "Activation of PmrA inhibits LpxT-dependent phosphorylation of lipid A promoting resistance to antimicrobial peptides", Molecular Microbiology, 76(6):1444-1460, Apr. 2010, Apr. 2010, 1444-1460.

Hutner, S. H. et al., "Some Approaches to the Study of the Role of Metals in the Metabolism of Microorganisms", Proceedings of the American Philosophical Society, 94(2):152-170, Apr. 1950, Apr. 1950, 152-170.

Jiang, M. Y. et al., "Post-adsorption process of Yb phosphate nano-particle formation by Saccharomyces cerevisiae", Geochimica et Cosmochimica Acta, 93:30-46, Sep. 2012, Sep. 2012, 30-46.

Kuroda, Kouichi et al., "Engineering of microorganisms towards recovery of rare metal ions", Applied Microbiology and Biotechnology, 87(1):53-60, Jun. 2010, Jun. 2010, 53-60.

Lo, Y. C. et al., "Recovery of High-Value Metals from Geothermal Sites by Biosorption and Bioaccumulation", Bioresource Technology, 160:182-190, May 2014, May 2014, 182-190.

Martin, Langdon J. et al., "Double-Lanthanide-Binding Tags: Design, Photophysical Properties, and NMR Applications", Journal of the American Chemical Society, 129(22):7106-7113, May 2007, May 2007, 7106-7113.

McDonald, J. C. et al., "Poly (dimethylsiloxane) as a Material for Fabricating Microfluidic Devices", Accounts of Chemical Research, 35(7):491-499, Apr. 2002, Apr. 2002, 491-499.

McGill, Ian, "Rare Earth Elements", Ullman's Encyclopedia of Industrial Chemistry, Wiley-VCH: Weinheim, 2000; pp. 183-228, 2000, 183-228.

Moore, Evan G. et al., "An Octadentate Luminescent Eu(III) 1,2-HOPO Chelate with Potent Aqueous Stability", Inorganic Chemistry, 46(14):5468-5470, Jul. 2007, Jul. 2007, 5468-5470.

Moriwaki, H et al., "Interactions of Microorganisms with Rare Earth Ions and their Utilization for Separation and Environmental Technology", Applied Microbiology and Biotechnology, 97(1):1-8, Jan. 2013, Jan. 2013, 1-8.

Nitz, M et al., "Structural Origin of the High Affinity of a Chemically Evolved Lanthanide-Binding Peptide", Angewandte Chemie International Edition, 43(28):3682-3685, Jul. 2004, Jul. 2004, 3682-3685.

Nomellini, John F. et al., "S-Layer-Mediated Display of the Immunoglobulin G-Binding Domain of Streptococcal Protein G on the Surface of Caulobacter crescentus: Development of an Immunoactive Reagent", Applied and Environmental Microbiology, 73(10):3245-3253, May 2007, May 2007, 3245-3253.

Onishi, H et al., "Spectrophotometric determination of zirconium, uranium, thorium and rare earths with arsenazo III after extractions with thenoyltrifluoroacetone and tri-n-octylamine", Talanta, 19(4):473-478, Apr. 1972, Apr. 1972, 473-478.

Ozaki, T et al., "Sorption Behavior of Europium(III) and Curium(III) on the Cell Surface of Microorganisms", Radiochimica Acta, 92(9-11):741-748, Nov. 2004, Nov. 2004, 741-748.

Parhi, P. K. et al., "Liquid-liquid Extraction and Separation of Total Rare Earth (RE) Metals from Polymetallic Manganese Nodule Leaching Solution", Journal of Rare Earths, 33(2):207-213, Feb. 2015, Feb. 2015, 207-213.

Park, Dan M. et al., "Bioadsorption of Rare Earth Elements through Cell Surface Display of Lanthanide Binding Tags", Environmental Science & Technology, 50(5):2735-2742, Feb. 2016, Feb. 2016, 2735-2742.

Park, Dan M. et al., "Modulation of Medium pH by Caulobacter crescentus Facilitates Recovery from Uranium-Induced Growth Arrest", Applied and Environmental Microbiology, 80(18):5680-5688, Sep. 2014, Sep. 2014, 5680-5688.

Patel, Jigar et al., "Genetic Engineering of Caulobacter crescentus for Removal of Cadmium from Water", Applied Biochemistry and Biotechnology, 160(1):232-243, Feb. 2009, Feb. 2009, 232-243.

Patel, Jigar et al., "Self-immobilization of Recombinant Caulobacter crescentus and Its Application in Removal of Cadmium from Water", Applied Biochemistry and Biotechnology, 162(4):1160-1173, Jan. 2010, Jan. 2010, 1160-1173.

Peelman, Sebastiaan et al., "Leaching of rare earth elements: Review of past and present technologies. In Rare Earths Industry Technological, Economic, and Environmental Implications", 1st ed.; Borges de Lima, I. F., W. L., Ed. 2015; pp. 319-334, 2015, 319-334.

Rahimi, Yasmeen et al., "Mechanism of Copper Induced Fluorescence Quenching of Red Fluorescent Protein, DsRed", Biochemical and Biophysical Research Communications, 370(1):57-61, May 2008, May 2008, 57-61.

Smit, John et al., "The S-layer of Caulobacter crescentus: Three-Dimensional Image Reconstruction and Structure Analysis by Electron Microscopy", Journal of Bacteriology, 174(20):6527-6538, Oct. 1992, Oct. 1992, 6527-6538.

(56) References Cited

OTHER PUBLICATIONS

Taggart, Ross K. et al., "Trends in the Rare Earth Element Content of U.S.-Based Coal Combustion Fly Ashes", Environmental Science & Technology, 50(11):5919-5926, May 2016, May 2016, 5919-5926.

Texier, Anne-Claire et al., "Selective Biosorption of Lanthanide (La, Eu, Yb) Ions by Pseudomonas Aeruginosa", Environmental Science & Technology, 33(3):489-495, Dec. 1998, Dec. 1998, 489-495.

Towett, Erick K. et al., "Quantification of Total Element Concentrations in Soils Using Total X-ray Fluorescence Spectroscopy (TXRF)", Science of the Total Environment, 463-464(1):374-388, Jul. 2013, Jul. 2013, 374-388.

Tsuruta, Takehiko, "Accumulation of Rare Earth Elements in Various Microorganisms", Journal of Rare Earths, 25(5):526-532, Oct. 2007, Oct. 2007, 526-532.

Utada, A. S. et al., "Monodisperse Double Emulsions Generated from Microcapillary Device", Science, 308(5721):537-541, Apr. 2005, Apr. 2005, 537-541.

Utturkar, Sagar M. et al., "Draft Genome Sequence for Caulobacter sp. Strain OR37, a Bacterium Tolerant to Heavy Metals", Genome Announcements, 1(3):1-2, May 2013, May 2013, 1-2.

Walker, Stephen G. et al., "Isolation and Comparison of the Paracrystalline Surface Layer Proteins of Freshwater Caulobacters", Journal of Bacteriology, 174(6):1783-1792, Mar. 1992, Mar. 1992, 1783-1792.

Wang, P et al., "Modeling Phase Equilibria and Speciation in Mixed-Solvent Electrolyte Systems: II. Liquid-Liquid Equilibria and Properties of Associating Electrolyte Solutions", Journal of Molecular Liquids, 125(1):37-44, Mar. 2006, Mar. 2006, 37-44.

Wang, Peiming et al., "A Speciation-Based Model for Mixed-Solvent Electrolyte Systems", Fluid Phase Equilibria, 203(1-2):141-176, Dec. 2002, Dec. 2002, 141-176.

Wei, Wei et al., "Simple Whole-Cell Biodetection and Bioremediation of Heavy Metals Based on an Engineered Lead-Specific Operon", Environmental Science & Technology, 48(6):3363-3371, Feb. 2014, Feb. 2014, 3363-3371.

Wu, Shurong et al., "Preparation and Thermal Behaviour of Rare Earth Citrate Hydrates", Journal of Thermal Analysis, 45(1-2):199-206, Jul. 1995, Jul. 1995, 199-206.

Wu, Zhuangchun et al., "Transparent, Conductive Carbon Nanotube Films", Science, 305(5688):1273-1276, Aug. 2004, Aug. 2004, 1273-1276.

Xie, Feng et al., "A Critical Review on Solvent Extraction of Rare Earths from Aqueous Solutions", Minerals Engineering, 56(1):10-28, Feb. 2014, Feb. 2014, 10-28.

Ye, Congwang et al., "Ceramic Microparticles and Capsules via Microfluidic Processing of a Preceramic Polymer", Journal of the Royal Society Interface, 7(4): S461-S473, May 2010, May 2010, S461-S473.

Zhuang, Wei-Qin et al., "Recovery of Critical Metals Using Biometallurgy", Current Opinion in Biotechnology, 33(1):327-335, Jun. 2015, Jun. 2015, 327-335.

Lee, Y., S., et al., "Microbial cell-surface display," TRENDS in Biotechnology vol. 21 No. 1, Jan. 2003.

Martin, J., L., et al., "Double-Lanthanide-Binding Tags: Design, Photophysical Properties, and NMR Applications," J. Am. Chem. Soc. 9 vol. 129, No. 22, 2007.

Moriwaki, H., et al., "Interactions of microorganisms with rare earth ions and their utilization for separation and environmental technology," Shinshu University, Faculty of Textile Science and Technology, Division of Applied Biology, 3-15-1.

Ryan, W., "Highly Sensitive Method for Detecting and Separating Pathogens using Paramagnetic," Biomedical Engineering Undergraduate Honors Theses (2013).

\* cited by examiner

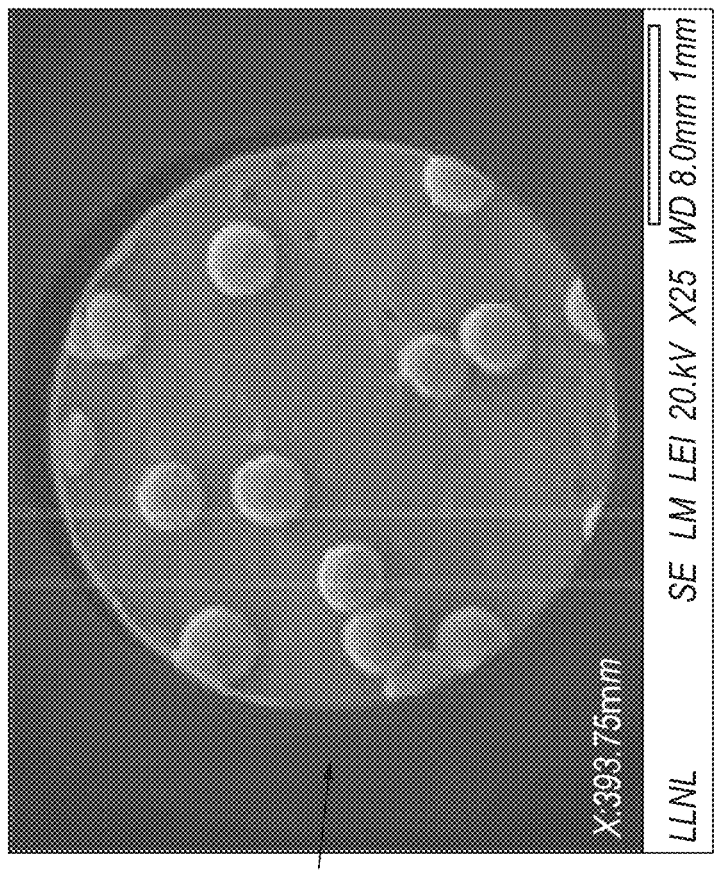
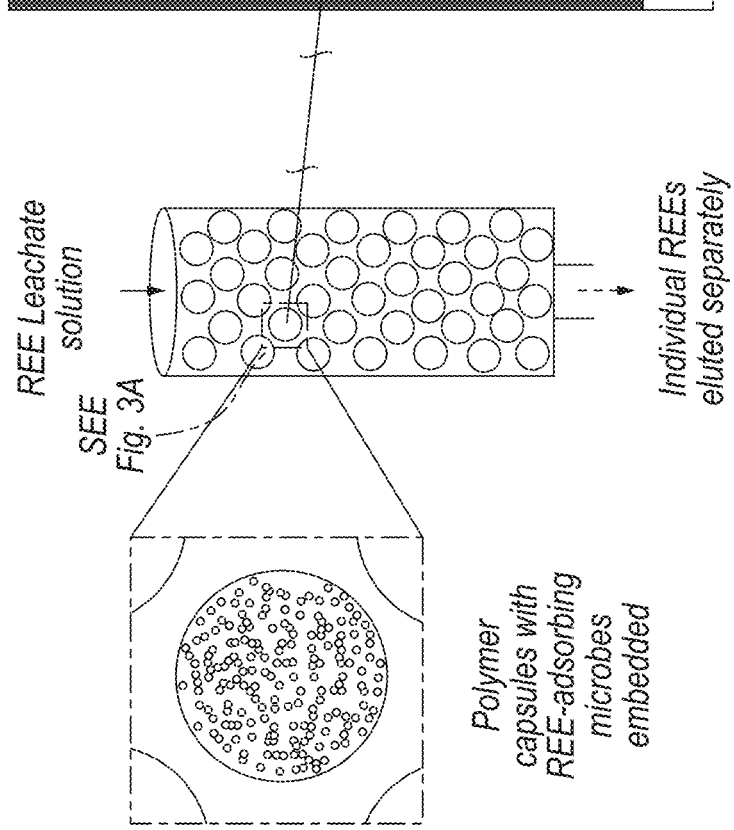
Fig. 3C
Fig. 3B
Fig. 3A

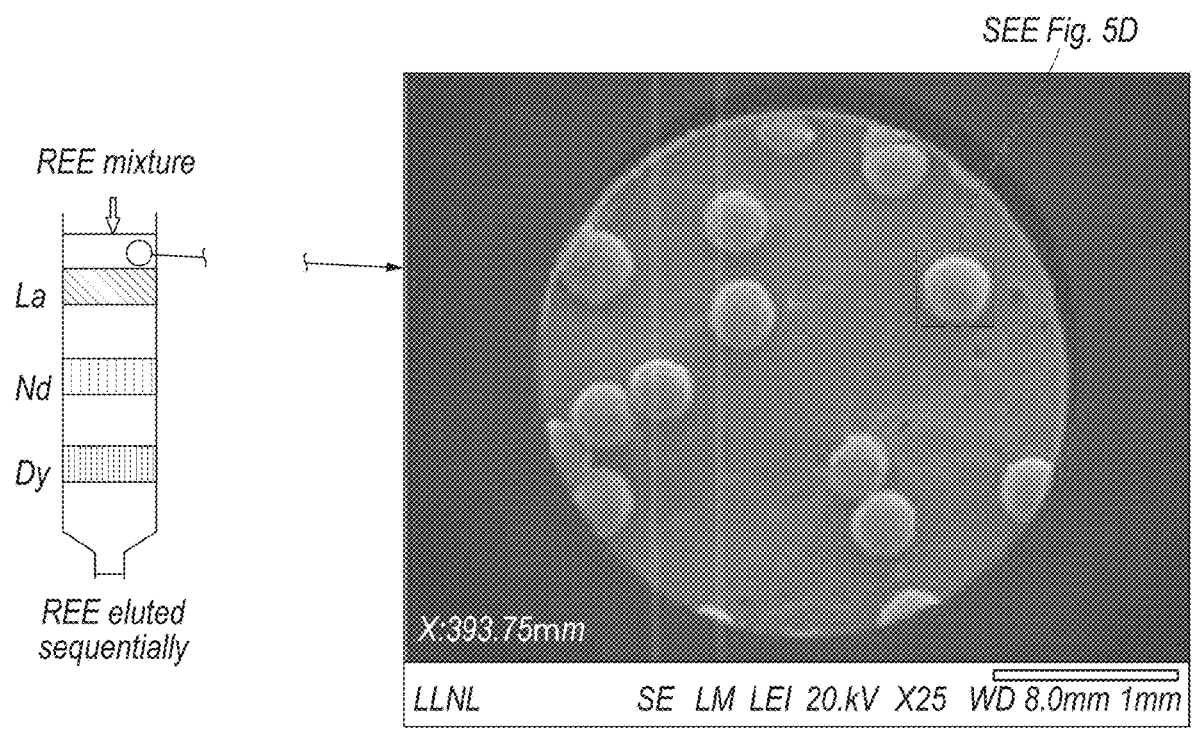
Fig. 5B
Fig. 5C
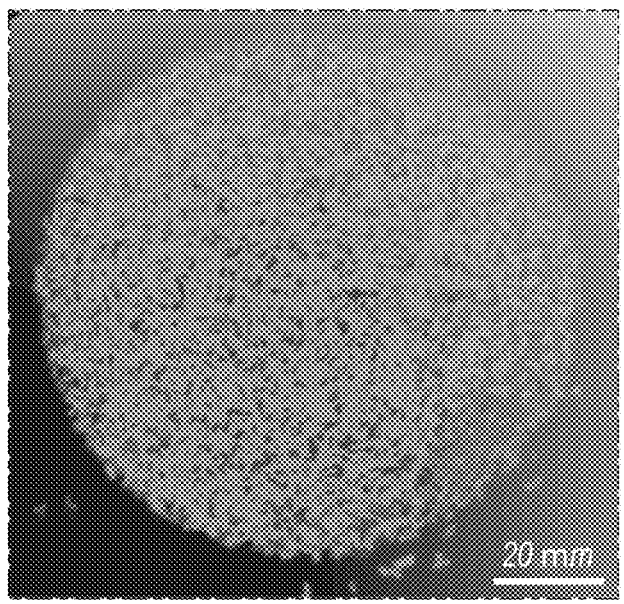
Fig. 5D

COMPOSITIONS AND METHODS OF USE THEREOF FOR RARE EARTH ELEMENT SEPARATION

STATEMENT REGARDING FEDERALLY SPONSORED RESEARCH

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Rare earth elements ("REEs") are mined from the Earth's crust. Because of their unique physical and chemical properties, these elements are crucial in a growing number of high-tech products, including high-performance magnets, lasers, computer memory, cell phones, catalytic converters, camera and telescope lenses, and green technologies such as wind turbines and hybrid vehicles, to name a few.

Many countries, including the United States produce REEs, but China has been the dominate producer of REEs, accounting for between 70-90% of the supply of the world's REEs. REEs are difficult to mine in part because it is unusual to find them in concentrations high enough for economical extraction. Use of GPS-controlled drills and Gamma-ray sampling allows geologists to identify higher REE-containing ore. The ore is often laced with radioactive materials such as thorium and current methods for the extraction and processing of REEs requires large amounts of carcinogenic toxins including organic solvents, ammonia salts, and strong acids. Leaching of metals has high energy/capital costs, high $CO_2$ emissions, and many negative health and environmental impacts.

As the demand for REEs continues to surge at a rapid rate, there remains a need for tools to help increase and diversify the supply of REEs, develop clean and low cost extraction processes, improve efficiencies, and recapture REEs through reuse and recycling. In particular, there is a need for the development of tools capable of preferentially separating REEs, especially from REE feedstocks in which the REE content is low relative to non-REEs with a focus on maximizing efficiency and minimizing waste.

SUMMARY

Methods and materials are provided for the preferential separation of REEs from REE-containing materials.

In some aspects, the present disclosure provides methods for preferentially separating rare earth elements (REEs) from a REE containing material comprising the steps of: (a) contacting genetically engineered microbes encoding at least one REE binding ligand with the REE containing material to form a microbe REE-complex; (b) introducing a tunable solution to the microbe REE-complex; and (c) separating at least a portion of the REEs from the microbe-REE complex based on affinity of the REE for the tunable solution compared to affinity of the REE for the at least one REE binding ligand, wherein at least a portion of the REEs are preferentially separated from the microbe-REE complex. In some embodiments, step (b) further comprises introducing a tunable solution to the microbe-REE complex, wherein the REEs are simultaneously adsorbed and desorbed from the at least one REE binding ligand. In some embodiments, the methods further comprise repeating steps (b) and (c) by introducing a modified tunable solution to the microbe-REE complex. In another embodiment, the modified tunable solution has a different concentration and/or is a different tunable solution as compared to the tunable solution in step (b). In yet another embodiment, the microbe-REE complex is formed in step (a) at a temperature between about 23° C. to about 100° C. In some embodiments, a temperature of the modified tunable solution is different than the temperature in step (a). In one embodiment, a concentration of the tunable solution is varied during the separating step (c).

In another aspect, the present disclosure provides methods for preparing a bead for REE separation comprising the steps of: (a) providing genetically engineered microbes comprising an exogenous nucleic acid sequence encoding at least one REE binding ligand; and (b) emulsifying the genetically engineered microbes with at least one other component to form a high cell density bead of the genetically engineered microbes; wherein the genetically engineered microbes are embedded within or on a surface of the bead.

In yet another aspect, the present disclosure provides beads for REE separation comprising genetically engineered microbes comprising an exogenous nucleic acid sequence encoding at least one REE binding ligand emulsified with at least one other component, wherein the bead has a high cell density of the genetically engineered microbes.

In some embodiments, the REEs are preferentially separated from the microbe-REE complex by tuning a concentration of the tunable solution. In another embodiment, the tunable solution comprises oxalate, an inorganic acid, an organic acid, a carbonate salt, a buffer, or any combination thereof.

In some embodiments, the methods preferentially separate individual REEs, groups of REEs, REEs adjacent to each other on the periodic table, or combination thereof. In another embodiment, at least one REE is separated relative to any other REE, any non-REE component, and/or to any other element in a purity of at least about 10%, at least about 15%, at least about 20%, at least about 30%, at least about 40%, at least about 50%, at least about 55%, at least about 60%, at least about 65%, at least about 70%, at least about 80%, at least about 85%, at least about 90%, at least about 95%, or at least about 100%.

In one embodiment, the at least one REE binding ligand comprises double lanthanide binding tags (dLBTs). In another embodiment, the at least one REE binding ligand comprises between 2 and 12 copies of dLBTs.

In some embodiments, the REE containing material is a low grade material, a high grade material, or a combination thereof.

In some embodiments, the high cell density bead of the genetically engineered microbes has a cell density of about $10^8$ cells/m L, $10^9$ cells/mL, $10^{10}$ cells/m L, $10^{11}$ cells/mL, $10^{12}$ cells/mL, $10^{13}$ cells/mL, $10^{14}$ cells/mL, $10^{15}$ cells/mL. In another embodiment, the bead has an adsorption capacity of about 3 to about 30 milligram (mg) of REE per gram (g) of the genetically engineered microbes. In yet another embodiment, the high cell density of the genetically engineered microbes is at least about 20 wt % or more of the total weight of the bead or least about 20 vol % or more of the total volume of the bead.

BRIEF DESCRIPTION OF THE DRAWINGS

FIGS. 3A and 3B are representative depictions of genetically engineered microbe beads in a column according to an embodiment of the disclosure.

FIG. 3C is a representative SEM image of the genetically engineered microbe beads of FIGS. 3A and 3B according to an embodiment of the disclosure.

FIG. 5B is a representative schematic of the genetically engineered microbes embedded into a hydrogel according to an embodiment of the disclosure.

FIGS. 5C and 5D are representative SEM and confocal images, respectively, of embedded genetically engineered microbes according to an embodiment of the disclosure.

DETAILED DESCRIPTION

Figure 1A:
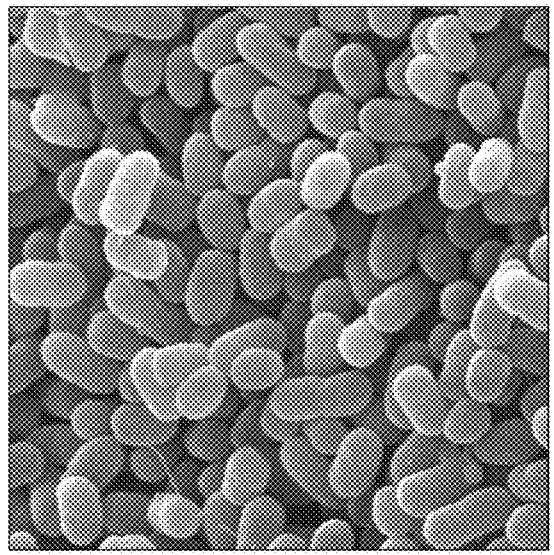
FIGS. 1A and 1B are representative scanning electron microscopy (SEM) images of surface binding peptides.

There is a growing interest for the development of new rare earth element (REE) extraction and separation technologies that maximize efficiency and minimize waste. REE extraction from solid feedstocks requires multiple steps, each with its own considerations to maximize efficiency and minimize waste. After acquiring the solid feedstock, the process begins with a leaching step using organic or mineral acids to release the REEs and other metals from the solid into solution. This leaching is typically not selective for REEs and results in the extraction of a wide range of competing metals such as non-REE metals to include alkali, alkaline, or other transition metals. REEs must then be separated from the competing metals. The extraction and purification process may be limited to separating total REEs from competing metals or, more commonly, aim to separate individual REEs from each other. This latter process is a significant technological challenge given the remarkably similar physicochemical properties of the REEs.

Liquid-liquid extraction (LLE) and ion exchange are the predominate technologies for REE separation and purification. LLE using targeted solvents is currently the industrial standard for REE purification. LLE involves two immiscible liquid phases, typically an aqueous and an organic phase. Dissolved metals selectively transfer between the phases at specific pH conditions. By repeating this process over many iterations, it is possible to achieve the purification of total REEs and even to separate and collect individual REEs. Unfortunately, there are several major drawbacks to this method, most notably the incompatibility with low-grade feedstocks and the use of large volumes of hazardous chemicals, which imposes an environmental burden that may, at least in part, offset the benefits of using REEs in green technologies. Ion exchange methods are used when a high degree of individual REE purity (>99.9999%) is desired; however, the technique is prohibitively expensive for large scale separation operations due to the high material cost. While this method may have niche uses in industry, for example when unusually high REE purity is required, it is not in a position to replace liquid-liquid extraction as the industrial standard for REE extraction.

Nontraditional REE resources, such as mine tailings, geothermal brines, end-of-life electronic consumer products, and coal byproducts are abundant and offer a potential means to diversify the REE supply chain. However, given the low REE content and high concentrations of competing metals present in these feedstocks, conventional REE-extraction and separation approaches, such as LLE, are prohibitive at an industrial scale. Therefore, the development of alternative technologies that enable efficient recovery of REEs from nontraditional feedstocks is highly desirable.

Unfortunately, prevailing technologies have limited selectivity toward REEs when exposed to a mixture of metals containing both REEs and non-REEs, especially when non-REE concentrations are much higher than those of REE. Thus, the low selectivity of these chemical adsorbents limits their applications towards REE feedstocks with high amounts of contaminating metals. Furthermore, the scalability of conventional approaches and corresponding efficacy to extract REEs from relevant feedstocks has not been examined.

The present disclosure relates to microbes for example, genetically engineered microbes for preferentially separating REEs from REE-containing materials. The use of the microbes for preferentially separating REEs from REE-containing materials as described herein overcome the technical, economic, and environmental limitations of conventional REE separation technologies.

After reading this description it will become apparent to one skilled in the art how to implement the invention in various alternative embodiments and alternative applications. However, all the various embodiments of the present invention will not be described herein. It will be understood that the embodiments presented here are presented by way of example only, and not limitation. As such, this detailed description of various alternative embodiments should not be construed to limit the scope or breadth of the present invention as set forth below.

The detailed description is divided into various sections only for the reader's convenience and disclosure found in any section may be combined with that in another section. Titles or subtitles may be used in the specification for the convenience of a reader, which are not intended to influence the scope of the present disclosure.

Unless the context indicates otherwise, it is specifically intended that the various features of the invention described herein can be used in any combination. Moreover, the disclosure also contemplates that in some embodiments any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Definitions

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

It must be noted that as used herein and in the appended claims, the singular forms "a," "an," and "the" include plural referents unless the context clearly dictates otherwise. Thus, for example, reference to "a microbe" includes a plurality of microbes.

As used herein the following terms have the following meanings:

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

The phrase "no or "substantially no" said refers to any competing metal that is present in an amount of less than about 0.0001%, less than about 0.001%, less than about 0.01%, less than about 0.1%, less than about 1%, less than about 5%, or less than about 10% of the total weight or volume of the purified REE material, composition, or eluted solution.

Also as used herein, "and/or" refers to and encompasses any and all possible combinations of one or more of the associated listed items, as well as the lack of combinations when interpreted in the alternative ("or").

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Microbes

Aspects of the disclosure provide microbes for use in separating REEs, including genetically engineered to express REE binding ligands, such as lanthanide binding tags (LBT). Suitable microbes, including suitable genetically modified microbes are described in US Publication No. 2018/0195147, which is incorporated by reference in its entirety.

REE are a group of seventeen chemical elements that includes yttrium and fifteen lanthanide elements. Scandium is found in most REE deposits and is often included.

TABLE 1

Rare Earth Elements

| Name | Symbol | Atomic Number |
|---|---|---|
| lanthanum | La | 57 |
| cerium | Ce | 58 |
| praseodymium | Pr | 59 |
| neodymium | Nd | 60 |
| promethium | Pm | 61 |
| samarium | Sm | 62 |
| europium | Eu | 63 |
| gadolinium | Gd | 64 |
| terbium | Tb | 65 |
| dysprosium | Dy | 66 |
| holmium | Ho | 67 |
| erbium | Er | 68 |
| thulium | Tm | 69 |
| ytterbium | Yb | 70 |
| lutetium | Lu | 71 |
| scandium | Sc | 21 |
| yttrium | Y | 39 |

The REE binding ligands can bind any of lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), scandium (Sc), yttrium (Y), or any combination thereof. The REE binding ligands can bind any of the elements in any oxidation state (e.g., $Ln^{1+}$, $Ln^{2+}$, $Ln^{3+}$, $Ln^{4+}$, etc.)

In some embodiments, the REE binding ligand (e.g., LBT) binds a lanthanide ion (e.g. a REE) with a binding affinity ($K_d$) of between about 1 nM and 500 µM, about 100 nM and 200 µM, or about 500 nM and 1 µM. In some embodiments, the $K_d$ is between about 500 nM and about 200 µM, about 1 µM and 200 µM, or about 50 µM and 100 µM. In some embodiments, the $K_d$ is about 1 µM, about 5 µM, about 10 µM, about 15 µM, about 30 µM, about 40 µM, about 50 µM, about 60 µM, about 70 µM, about 80 µM, about 90 µM, about 100 µM, about 110 µM, about 120 µM, about 130 µM, about 140 µM, about 150 µM, about 160 µM, about 170 µM, about 180 µM, about 190 µM, about 200 µM, or more. In some embodiments, the $K_d$ is in the µM range. In other embodiments, the $K_d$ is in the nM range. In still other embodiments, the $K_d$ is in the µM range. Affinity can be determined by any suitable means known to one of skill in the art. Non-limiting examples include, titration with REE and detection using fluorescence, circular dichroism, NMR or calorimetry. In the case of tightly binding sequences, it may be necessary to employ competition experiments.

Compositions

The present disclosure also provides composition comprising an amount of the microbes for example, genetically modified microbes.

Biosorption Systems

Also provided are systems (i.e., biosorption/adsorption media) for REE extraction and preferential separation comprising an amount of the microbes. In addition, provided herein are cell-free systems for use in the same.

In some embodiments, the microbes are attached to a solid support, for example, a column, a membrane, a bead, or the like. The solid support can be any suitable composition known to one of skill in the art including, for example, a polymer, alginate, acrylamide, regenerated cellulose, cellulose ester, plastic, or glass.

These biosorption media, which include, for example, biofilm, microbe beads, and carbon nanotube embedded membranes can be used for adsorption under continuous flow. It is contemplated that microbe immobilization in biosorption media for use in flow through setups allows for complete (or substantially complete) separation of REEs from REE-containing mixed metal solutions in a single step and, for example, without the need of centrifugation, filtration, or both.

In one embodiment, the microbes are immobilized via the formation of a biofilm. A biofilm is a layer of microorganisms that are attached to a surface. For biofilm formation, microbes having the distinctive ability to self-immobilize on supported solid surfaces, for example, *Caulobacter* may be used. *Caulobacter* forms uniform, high-density biofilms owing to a strongly adhesive organelle, a holdfast that is present at the distal tip of the stalk. In some embodiments, the biofilms are monolayers. The biofilms can be housed within a bioreactor including, for example, a spiral-sheet bioreactor, a fiber brush bioreactor, or other supported vehicles suspended in the bioreactor. In other embodiments, the biofilms are three-dimensional. 3D mushroom-like structures are observed to form interspersed with monolayer biofilms. (Entcheva-Dimitrov P. et al., (2004) *J of Bacteriology* 186(24):8254-8266). These 3D structures can promote cell detachment, cause clogging and disruption of solution diffusion and transport, which are undesirable for REE adsorption. In some embodiments, to minimize 3D structures, a flgH microbial mutant that cannot make a functional flagellum can be generated. (Entcheva-Dimitrov P. et al., (2004) *J of Bacteriology* 186(24):8254-8266). It is contemplated that knocking out the flgH gene will eliminate mushroom-like structures, promote monolayer biofilm formation, and therefore enhance REE adsorption.

Microbes can be immobilized on any suitable supporting material for optimal microbe attachment (e.g., fast, stable) known to one of skill in the art. Non-limiting examples of supporting material include carbon film, glass, steel, Teflon, polyethylene and the like. Growth media, temperature, inoculum size, incubation temperature, or any combination thereof can be varied to determine the optimal conditions for biofilm formation on each supporting material. In some embodiments, holdfast-containing *Caulobacter* strains will facilitate biofilm formation.

In one embodiment, the genetically engineered microbes are bound (i.e., embedded) within or to the surface of a bead. In some embodiments, the bead is a polymer. Suitable polymers include PEG (e.g., ~10% PEG), alginate (e.g., ~2% calcium alginate), and acrylamide (e.g., ~10% polyacrylamide). In other embodiments the beads are glass, plastic, or steel.

In one embodiment, the microbes are immobilized through fabrication of micro beads. The synthesis and fabrication of micro bead in the 10 to 1000's microns size range for material encapsulation, storage and release have received significant attention in the past years for different applications, in order to isolate and protect the core materials from the surrounding environment. For example, encapsulation can protect enzymes from denaturing by solvents, shield probiotic bacteria from high temperature and digestive system, and protect chemicals from deteriorating due to oxidation and moisture with an inert matrix or shell. Moreover, encapsulations can allow and improve the controlled release of the encapsulated ingredient or immobilize living cells for controlled growth. As used herein, the term "encapsulate" is used interchangeable with the term "embed."

Any suitable microencapsulation techniques known to one of skill in the art can be used to encapsulate the microbes of the present disclosure. In some embodiments, polymers such as acrylamide, silicone, and acrylate are used. Polymers have become the primary shell/matrix material used in this area because of the high solubility in organic solvents, easy and versatile formation, crosslinkable nature, sufficient strength and wide variety of chemistries.

The genetically engineered microbes can be provided in a reactor. Reactors can be configured in any suitable arrangement known to one of skill in the art, for example, spiral sheet and fiber brush, column purification, and filtration systems. Operation parameters and modeling that can be optimized by one of skill in the art include, for example, flow rate, extraction efficiency and product purification, solution conditioning (e.g., calcium addition), and surface complexation modeling (SCM) and performance optimization and prediction.

Biosorption is a chemical process based on a variety of mechanisms such as adsorption, absorption, ion exchange, surface complexation, and precipitation. When coupled with a material of biological origin such as microbes or biomass, this material is referred to as biosorption material. A biosorption material can for example, bind to REEs and separate them from REE containing materials (e.g., feedstocks). Provided herein are biosorption materials comprising microbes for preferentially separating REEs from REE containing material. REE extraction and preferential separation comprising an amount of the microbes. In addition, provided herein are cell-free systems for use in the same.

In some embodiments, the biosorption material is a bead and/or capsule. In some embodiments, the bead and/or capsule is suitable for the separation of REEs. In some embodiments, the bead and/or capsule comprises genetically engineered microbes comprising an exogenous nucleic acid sequence encoding at least one REE binding ligand. In some embodiments, the biosorption material is a micro bead. As used herein, the term "microbe capsule" is used interchangeably with "microbe bead" and the term "capsule" is used interchangeably with "bead."

In other embodiments, the disclosure provides methods of preparing a bead for REE separation. In some embodiments, the methods for preparing a bead for REE separation comprise: (a) providing genetically engineered microbes comprising an exogenous nucleic acid sequence encoding at least one REE binding ligand; and (b) emulsifying the genetically engineered microbes with at least one other component to form a high cell density bead of the genetically engineered microbes; wherein the genetically engineered microbes are embedded within or on a surface of the bead.

In some embodiments, the bead has a high cell density of genetically engineered microbes. It is contemplated that a high cell loading can act, at least in part, to enhance the saturation capacity of the biosorption material by increasing the number of available REE binding ligands. An increased number of REE binding ligands leads to a larger percentage of REEs from the REE-containing material that complex with the REE binding ligands to form a microbe-REE complex (e.g., increased saturation capacity). In some embodiments, the increase in saturation capacity correlates with an increase in adsorption capacity (i.e., an increase in the number of REEs that complex with REE binding ligands per unit volume or unit mass of the REE-containing material). It is contemplated that an increased saturation and adsorption capacity obviates the need from additional and energy exhaustive steps such as centrifugation and filtration in the process of separating REEs.

In some embodiments, the high cell density of the microbes is about $10^8$ cells per milliliter (cells/mL), $10^9$ cells/mL, $10^{10}$ cells/mL, $10^{11}$ cells/mL, $10^{12}$ cells/mL, $10^{13}$ cells/mL, $10^{14}$ cells/mL, $10^{15}$ cells/mL, or any combination thereof, of the total volume of the bead. In some embodiments, the bead for REE separation has a high cell density between about $10^8$ cells/mL to $10^{15}$ cells/mL, about $10^8$ cells/mL to about $10^{11}$ cells/mL, about $10^9$ cells/mL to about $10^{13}$ cells/mL, about $10^{10}$ cells/mL to about $10^{12}$ cells/mL, about $10^8$ cells/mL to about $10^{13}$ cells/mL, about $10^{11}$ cells/mL to about $10^{15}$ cells/mL, or about $10^{10}$ cells/mL to about $10^{15}$ cells/mL.

In some embodiments, the a high cell density of the microbes is at least about 20 weight percent (wt %), at least about 25 wt %, at least about 30 wt %, at least about 35 wt %, at least about 40 wt %, at least about 45 wt %, at least about 50 wt %, at least about 55 wt %, at least about 60 wt %, at least about 65 wt %, at least about 70 wt %, at least about 75 wt %, at least about 80 wt %, at least about 85 wt %, at least about 90 wt %, at least about 95 wt %, or more of the total weight of the bead or at least about 20 volume percent (vol %), at least about 25 vol %, at least about 30 vol %, at least about 35 vol %, at least about 40 vol %, at least about 45 vol %, at least about 50 vol %, at least about 55 vol %, at least about 60 vol %, at least about 65 vol %, at least about 70 vol %, at least about 75 vol %, at least about 80 vol %, at least about 85 vol %, at least about 90 vol %, at least about 95 vol % or more of the total volume of the bead.

In some embodiments, the high adsorption capacity of the microbes is at least about 1 milligram (mg), at least about 2 mg, at least about 3 mg, at least about 4 mg, at least about 5 mg, at least about 6 mg, at least about 7 mg, at least about 8 mg, at least about 9 mg, at least about 10 mg, at least about 11 mg, at least about 12 mg, at least about 13 mg, at least about 14 mg, at least about 15 mg, at least about 16 mg, at least about 17 mg, at least about 18 mg, at least about 19 mg, at least about 20 mg, at least about 21 mg, at least about 22 mg, at least about 23 mg, at least about 24 mg, at least about 25 mg, at least about 26 mg, at least about 27 mg, at least about 28 mg, at least about 29 mg, at least about 30 mg, at least about 31 mg, at least about 32 mg, at least about 34 mg, at least about 35 mg, at least about 36 mg, at least about 37 mg, at least about 38 mg, at least about 39 mg, at least about 40 mg, at least about 41 mg, at least about 42 mg, at least about 43 mg, at least about 44 mg, at least about 45 mg, at least about 46 mg, at least about 47 mg, at least about 48 mg, at least about 49 mg, or at least about 50 mg of REE per gram (g) of microbes.

In some embodiments, the high adsorption capacity of the microbes is at least about 1 milligram (mg), at least about 2 mg, at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 110 mg, at least about 115 mg, at least about 120 mg, at least about 125 mg, at least about 130 mg, at least about 135 mg, at least about 140 mg, at least about 145 mg, at least about 150 mg, at least about 155 mg, at least about 160 mg, at least about 165 mg, at least about 170 mg, at least about 175 mg, at least about 180 mg, at least about 185 mg, at least about 190 mg, at least about 195 mg, at least about 200 mg, at least about 205 mg, at least about 210 mg, at least about 215 mg, at least about 220 mg, at least about 225 mg, at least about 230 mg, at least about 235 mg, at least about 240 mg, at least about 245 mg, or at least about 250 mg of REE per gram (g) of microbes. In some embodiments, the microbes have an adsorption capacity between about 3 to about 30 mg of REE per g of microbes.

In another embodiment, the microbes are encapsulated within and/or on a surface of the bead. When the microbes are encapsulated within and/or on the surface of the bead, the beads are able to efficiently bind the REEs at the least one REE binding ligand by increasing the accessibility REE binding ligands for the REEs. Once the REE-containing material is flowed on and/or through the bead, the REE binding ligands are able to capture the REEs both within and on the surface of the bead, which optimizes the adsorption capacity of the bead by increasing the ratio of available binding sites (i.e., binding ligands) to total volume of the bead.

In some embodiments, the beads are porous. The porous beads enable the flow of the REE containing material to contact not only the exterior surface, but also, the interior surface of the bead thereby increase the saturation and absorption capacity of the bead for the REEs (i.e., increased accessibility). In some embodiments, the beads have a pore diameter of at least about 0.10 nm, at least about 1.0 nm, at least about 10 nm, at least about 50 nm, at least about 100 nm, at least about 150 nm, at least about 200 nm, at least about 250 nm, at least about 300 nm, at least about 350 nm, at least about 400 nm, at least about 450 nm, at least about 500 nm, at least about 550 nm, at least about 600 nm, at least about 650 nm, at least about 700 nm, at least about 750 nm, at least about 800 nm, at least about 850 nm, at least about 900 nm, at least about 950 nm, or at least about 1000 nm. In some embodiments, the bead has a pore diameter between about 1.0 nm to about 500 nm, about 0.10 nm to about 10 nm, about 150 nm to about 1000 nm, about 300 nm to about 600 nm, about 200 nm to about 800 nm, about 300 nm to about 500 nm, about 500 nm to about 1000 nm, or about 600 nm to about 800 nm.

In yet another embodiment, the bead further comprises at least one other component emulsified with the microbes. The emulsified bead consists of a dispersion of the microbes with the at least one other component, wherein at least two of the constituents of the emulsion are not miscible and/or soluble with each other (i.e., aqueous and oil components). In some embodiments, the emulsifying step comprises mixing the microbes and at least one other component. In some embodiments, the beads are formulated as emulsions with the microbes and at least one other component.

In some embodiments, an emulsion method is used to encapsulate (i.e., embed) the microbes into the beads. Conventionally biosorption materials comprising microbes are formed through microfluidic processes (i.e., a microfluidic platform). However, microfluidic processes result in beads with unsatisfactory cell loadings compositions (i.e., suspensions) comprising a high cell density clog the capillaries associated with using microfluidic processes. The emulsion method overcomes these challenges by obviating the need for capillaries. For example, in an exemplary embodiment of the present disclosure, a high cell density suspension of the microbes, PEDGA, ethyl (2,4,5-trimethylbenzoyl) phenyl phosphinate (TPO-L), and polydimethylsiloxane (PDMS) oil are emulsified by vigorous shaking. Following emulsification, microdroplets of the biosorption material are polymerized using UV light, resulting in the formation of the beads for REE separation. This method enables the formation of beads with a high cell density and a corresponding high REE adsorption capacity, that are 20 times greater than beads made through conventional microfluidic processes. This method also provides a high-throughput generation of the beads, enabling the formation of multiple beads at a given time, corresponding to a high-throughput production that is 10 times more efficient than conventional microfluidic methods. Accordingly, the emulsion method provides a scalable, inexpensive method of embedding microbes within the beads (e.g., PEDGA beads).

In some embodiments, the disclosure provides methods of preparing a bead for REE separation that is cost-effective by precluding the need from time consuming and expensive chemical synthesis. The microbes have an innate ability to synthesize and immobilize selective bio-absorbents (i.e., REE binding ligands) as they grow and duplicate. The innate ability to grown and duplicate bio-absorbents prevents the need for costly chemical synthesis to produce the bio-absorbents required for conventional REE separation processes.

In some embodiments, the emulsification method for preparing beads comprising microbes results in the formation of beads with a high stability. In some embodiments, the beads are stable for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 1 year.

In some embodiments, the at least one other component is a polymer, photoinitiator, an oil, or any combination thereof.

In some embodiments, the at least one other component is a polymer, wherein polymer refers to any component that has a molecular structure comprised of similar repeating units bonded together. In some embodiments, the polymer can be an oligomer, monomer, or mixtures thereof. Non-limiting examples of polymers include styrene, methacrylate, vinyl alcohol, polyisobutylene, glycercol, polypropylene, PEDGA, and polyethylene glycol dimethacrylate.

In some embodiments, the at least one other component is a photoinitiator, wherein a photoinitiator refers to any component that reacts, fragments, and/or creates reactive species (e.g., free radicals, cations, or ions) when exposed to radiation (e.g., ultra-violet (UV) or visible light). A function of the photoinitiator is to initiate photopolymerization of the polymer upon irradiation with light. In one embodiment, the photoinitiator absorbs light and initiates the photopolymerization of the polymer to enable the formation of the bead. In some embodiments, the photoinitiator is a liquid type photoinitiator such as ethyl (2,4,5-trimethylbenzoyl) phenyl phosphinate (TPO-L), bis-acylphosphine oxide (BAPO), 2-hydroxy-2-methyl propiophenone, methylbenzoyl formate, isoamyl 4-(dimethylamino) benzoate, 2-ethyl hexyl-4-(dimethylamino) benzoate, or diphenyl(2,4,6-trimethylbenzoyl) phosphine oxide (TPO). Additional, non-limiting examples of suitable photo-initiators include 1-hydroxycyclohexyl phenyl ketone (Irgacure 184), 2,2-dimethoxy-2-phenylacetophenone (Irgacure 651), and 2-methyl-1-[4-(methylthio) phenyl]-2-(4-morpholinyl)-1-propanone (Irgacure 907), hydroxyacetophenone, phosphineoxide, benzophenone, and lithium phenyl-2,4,6-trimethylbenzoylphosphinate (LAP).

In some embodiments, the at least one other component is an oil, wherein oil refers to any component that is immiscible with an aqueous component (i.e., water). In some embodiments, the oil component comprises mixtures of two or more oils. Non-limiting examples of oils suitable for forming the emulsion formulations of the present disclosure include natural oils such as almond oil, coconut oil, cod liver oil, corn oil, cottonseed oil, castor oil, olive oil, palm oil, peanut oil, peppermint oil, rose oil, safflower oil, sesame oil, soybean oil, sunflower oil and vegetable oil and synthetic oils such as triethylglycerol, diethylglycerol, and PDMS.

In some embodiments, the polymer, oil component, and/or photoinitiator is present in at least about 5 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 30 wt %, about 40 wt %, about 50 wt %, about 60 wt %, about 70 wt %, about 80 wt %, about 90 wt %, about 95 wt % or more of the total weight of the bead or least about 5 vol %, about 10 vol %, about 11 vol %, about 12 vol %, about 13 vol %, about 14 vol %, about 15 vol %, about 16 vol %, about 17 vol %, about 18 vol %, about 19 vol %, about 20 vol %, about 30 vol %, about 40 vol %, about 50 vol %, about 60 vol %, about 70 vol %, about 75 vol %, about 80 vol %, about 85 vol %, about 90 vol %, about 95 vol %, or more of the total volume of the bead.

Methods

Also provided are methods of using the microbes, for example genetically modified microbes to preferentially separate REE from REE-containing materials from a REE (e.g., Tb or Eu) containing material.

In one aspect provided herein are methods for preferentially separating REEs from a REE-containing material comprising the steps of: (a) contacting genetically engineered microbes encoding at least one REE binding ligand with the REE-containing material to form a microbe REE-complex; (b) introducing a tunable solution to the microbe REE-complex; and (c) separating at least a portion of the REEs from the microbe-REE complex based on affinity of the REE for the tunable solution compared to affinity of the REE for the at least one REE binding ligand, wherein at least a portion of the REEs are preferentially separated from the microbe-REE complex. In some embodiments, the steps described are executed once. In other embodiments, the steps or a portion of the steps are executed more than once, for example, 2, 3, 4, 5, or more times. In some embodiments, the steps or portions of the steps are executed more than once with more than one REE-containing material, for example with 1, 2, 3, 4, 5, or more REE-containing materials.

In some embodiments, the steps or portions of the steps are repeated until at least about 100%, at least about 90%, at least about 80%, at least about 70%, at least about 60%, at least about 50%, at least about 40%, at least about 30%, at least about 20%, or at least about 10% of the REEs are separated from the microbe-REE complex.

In some embodiments, the microbe REE-complex is formed at a temperature between about 23 degrees Celsius (° C.) to about 100° C. in step (a). In some embodiments, the REE complex is formed at a temperature of about 150° C., about 145° C., about 140° C., about 135° C., about 130° C., about 125° C., about 120° C., about 115° C., about 110° C., about 105° C., about 100° C., about 95° C., about 90° C., about 85° C., about 80° C., about 75° C., about 70° C., about 65° C., about 60° C., about 55° C., about 50° C., about 45° C., about 40° C., about 35° C., about 30° C., or about 25° C.

In some embodiments, the tunable solution is tuned by varying parameters such as concentration (e.g., change the amount of solvent), pH (e.g., changing the basicity or acidity), temperature, or pressure of the solution to preferentially separate the REEs. In some embodiments, the REEs are preferentially separated from the microbe-REE complex by tuning the concentration, pH, temperature, or pressure of the tunable solution. In some embodiments, the tunable solution is varied by a gradient of the parameters (i.e., concentration, pH, temperature, or pressure) to preferentially elute the REEs. For example, in some embodiments, the tunable solution is tuned during the separation step (c) by initially adding of solution with a first concentration followed by changing the concentration of the tunable solution to a second concentration, wherein the second concentration is higher or lower than the first concentration. In some embodiments, the gradient of the parameters further comprises a third, fourth, fifth, sixth, seventh, eighth, ninth, tenth, or more concentration, pH, temperature, or pressure. In some embodiments, the parameter is varied incrementally, wherein the parameter is set to a specific concentration, pH, temperature, or pressure until the REEs are preferentially separated. In some embodiments, the gradient is continuous, wherein the parameter is constantly changing until the REEs are preferentially separated.

In some embodiments, the concentration of the tunable solution is between about 0 mM to about 10 mM, about 0.1 mM to about 10 mM, about 0 mM to about 15 mM, about 0.1 mM to about 15 mM, about 0 mM to about 20 mM, about 0.1 mM to about 20 mM, about 0 mM to about 25 mM, about 0.1 mM to about 25 mM, about 0 mM to about 30 mM, about 0.1 mM to about 30 mM, about 0 mM to about 35 mM, about 0.1 mM to about 35 mM, about 0 mM to about 40 mM, about 0.1 mM to about 40 mM, about 0 mM to about 45 mM, about 0.1 mM to about 45 mM about 0 mM to about 50 mM, about 0.1 mM to about 50 mM, about 0 mM to about 55 mM, about 0.1 mM to about 55 mM, about 0 mM to about 60 mM, about 0.1 mM to about 60 mM, about 0 mM to about 70 mM, about 0.1 mM to about 70 mM, about 0 mM to about 75 mM, about 0.1 mM to about 75 mM, about 0 mM to about 80 mM, about 0.1 mM to about 80 mM, about 0 mM to about 85 mM, about 0.1 mM to about 85 mM, about 0 mM to about 90 mM, about 0.1 mM to about 90 mM, about 0 mM to about 95 mM, about 0.1 mM to about 95 mM, about 0 mM to about 100 mM, about 0.1 mM to about 100 mM, about 0 mM to about 110 mM, about 0.1 mM to about 110 mM, about 0 mM to about 120 mM, about 0.1 mM to about 120 mM, about 0 mM to about 125 mM, about 0.1 mM to about 125 mM, about 0 mM to about 130 mM, about 0.1 mM to about 130 mM, about 0 mM to about 135 mM, about 0.1 mM to about 135 mM, about 0 mM to about 140 mM, about 0.1 mM to about 140 mM, about 0 mM to about 145 mM, about 0.1 mM to about 145 mM, about 0 mM to about 150 mM, about 0.1 mM to about 150 mM, about 0 mM to about 1 M, about 0.1 mM to about 1 M, about 0 mM to about 10 M, about 0.1 mM to about 10 M, about 0 mM to about 100 M, about 0.1 mM to about 100 M, about 0 mM to about 200 M, about 0.1 mM to about 200 M, about 0 mM to about 300 M, about 0.1 mM to about 300 M, about 0 mM to about 400 M, about 0.1 mM to about 400 M, about 0 mM to about 500 M, about 0.1 mM to about 500 M, about 0 mM to about 600 M, about 0.1 mM to about 600 M, 0 mM to about 700 M, 0.1 mM to about 700 M, about 0 mM to about 800 M, about 0.1 mM to about 800 M, about 0 mM to about 900 M, about 0.1 mM to about 900 M, about 0 mM to about 1000 M, about 0.1 mM to about 1000 M, or any range in between.

In some embodiments, the pH of the tunable solution is between about 0 to about 14, about 1 to about 13, about 1 to about 12, about 2 to about 10, about 3 to about 6, about 4 to about 8, about 1 to about 7, about 1 to about 6, about 2 to about 6, about 2 to about 7, about 2 to about 10, about 2 to about 14, about 3 to about 11, about 5 to about 10, about 4 to about 13, about 8 to about 14, or about 7 to about 13, or any range in between.

In some embodiments, the temperature of the tunable solution is between about 25° C., to about 90° C., about 10° C. to about 40° C., about 15° C. to about 70° C., about 25°

C. to about 50° C., about 0° C. to about 100° C., about 20 to about 60° C., about 30 to about 90° C., about 40 to about 90° C., about 25° C. to about 40° C., about 25° C. to about 80° C., or any range in between. In another, embodiment, the temperature of the tunable solution is different than the temperature in which the REE-complex is formed. For example, in some embodiments the temperature of the tunable solution is about 2 degrees higher or lower, about 5 degrees higher or lower, about 10 degrees higher or lower, about 15 degrees higher or lower, about 20 degrees higher or lower, about 25 degrees higher or lower, about 30 degrees higher or lower, about 35 degrees higher or lower, about 40 degrees higher or lower, about 40 degrees higher or lower than the temperature in which the REE-complex is formed.

In some embodiments, the pressure of the tunable solution is between 1 standard atmosphere pressure unit (atm) to about 10 atm, about 1 atm to about 15 atm, about 1 atm to about 20 atm, about 1 atm to about 25 atm, about 1 atm to about 20 atm, or any range in between.

In some embodiments, the tunable solution is an ionic solution. For example, in some embodiments, the ionic solution is an anionic solution or a cationic solution. In some embodiments, the tunable solution comprises oxalate, an inorganic acid, an organic acid, a carbonate salt, a buffer, an inorganic base, an organic base, a chelating agent or any combination thereof.

In some embodiments, the tunable solution comprises an oxalate which includes any compound with the general formula of $C_2O_4^{-2}$. Non-limiting examples of oxalates include sodium oxalate, potassium oxalate, dimethyl oxalate, calcium oxalate, diphenyl oxalate, or potassium ferrioxalate.

In some embodiments, the tunable solution comprises inorganic acids which include any acidic compound derived from one or more inorganic compounds (i.e., do not contain hydrogen-carbon (H—C) bonds) or containing inorganic elements. Non-limiting examples of inorganic acids include hydrogen sulfide ($H_2S$), phosphoric acid ($H_3PO_4$), hydrogen chloride (HCl), nitric acid ($HNO_3$), or sulfuric acid ($H_2SO_4$).

In some embodiments, the tunable solution comprises organic acids which include any acidic compound derived from an organic compound (i.e., includes H—C bonds) or containing organic elements. Organic acids include carboxylic acids (i.e., $CO_2H$ substituent), sulfonic acids (i.e., $SO_2OH$), or alcohols (i.e., OH substituent). Non-limiting examples of organic acids include lactic acid ($CH_3CH(OH)CO_2H$), acetic acid ($CH_3CO_2H$), formic acid ($HCO_2H$), citric acid ($C_6H_8O_7$), oxalic acid ($C_2H_2O_4$), uric acid ($C_5H_4N_4O_3$), ascorbic acid ($C_6H_8O_6$), benzenesulfonic acid ($C_6H_6O_3S$), p-toluenesulfonic acid ($C_7H_8O_3S$), methanesulfonic acid ($CH_4O_3S$), or triflic acid ($CF_3SO_3H$).

In some embodiments, the tunable solution comprises a buffer which includes any solution that resists changes in pH (i.e., pH changes very little when a strong acid or base is added) when an acid or base is added to said solution. Buffer solutions are aqueous solutions comprised a weak acid and its conjugate base or a weak base and its conjugate acid. In some embodiments, a buffer solution is used to keep the pH of the solution constant during the separation of the REEs from the REE-containing material. Non-limiting examples of buffer solutions include phosphate, 2-ethanesulfonic acid (MES), ethylenediaminetetraacetic acid (EDTA), saline, phosphate buffered saline (PBS), tris/borate/EDTA (TES), citrate, tris/acetate/EDTA (TAE).

In some embodiments, the tunable solution comprises carbonate salts include which includes any compound that is a salt of carbonic acid ($H_2CO_3$) and with the general formula of $CO_3^{-2}$ or $HCO_3^{-}$. Non-limiting examples of carbonates include sodium carbonate ($Na_2CO_3$), sodium bicarbonate ($NaHCO_3$), lithium carbonate ($Li_2CO_3$), lithium bicarbonate ($LiHCO_3$), potassium carbonate ($K_2CO_3$), potassium bicarbonate ($KHCO_3$), magnesium carbonate ($MgCO_3$), magnesium bicarbonate ($Mg(HCO_3)_2$), calcium carbonate ($CaCO_3$), calcium bicarbonate ($Ca(HCO_3)_2$), ammonium carbonate (($NH_4)_2CO_3$), or ammonium bicarbonate (($NH_4)HCO_3$).

In some embodiments, the tunable solution comprises inorganic bases which includes any basic compound derived from one or more inorganic compounds (i.e., do not contain H—C bonds) or inorganic elements. Non-limiting examples of inorganic bases include sodium hydroxide (NaOH), ammonium hydroxide ($NH_4OH$), sodium carbonate ($Na_2CO_3$), sodium bicarbonate ($NaHCO_3$), calcium hydroxide ($Ca(OH)_2$), potassium cyanide (KCN), potassium hydroxide (KOH), calcium oxide (CaO), or calcium carbonate ($CaCO_3$).

In some embodiments, the tunable solution comprises organic bases which includes any basic compound derived from an organic compound (i.e., includes H—C bonds) or containing organic elements. Non-limiting examples of organic bases include pyridines, alkanamines, imidazoles, benzimidazoles, histidines, phosphazene, or hydroxides.

In some embodiments, the tunable solution comprises chelating agents which includes any compound comprises of functional groups capable of binding non-REE metal or a REE. Non-limiting examples of chelating agents include EDTA, citrate, or dimercaprol.

Preferential Separation

Preferential separation of REEs from REE containing materials is a crucial for the development of technologies such as batteries, magnets, and electronics, however the similarity in the chemical properties of REEs makes them exceedingly challenging to separate from each other as well as from other non-REEs. Prevailing technologies are hampered by low selectivity towards REEs, particular when the REEs are in the presence of a mixture of competing metals such as non-REEs (e.g., alkali, alkaline, and other transition metals). Even more challenging, is the separation of REEs from the competing metals wherein the competing metals are present at much higher concentration than the REEs. Due to the innate challenges in separating REEs, conventional technologies are limited in their ability to separate REEs in high purity and further has, prevented the development of systems capable of preferentially separating REEs on an industrial, bulk scale. The present disclosure provides methods for the preferential separation of REEs with a high selectivity, high efficiency, and at a low cost, characteristics that each lend themselves towards a system capable of separating REEs on a large, industrial scale. In some embodiments, the methods for preferentially separating REEs from a REE-containing material include separating individual REEs or groups of REEs from other REEs or non-REEs. Preferential separation an individual REE refers to the isolation of an REE (e.g., La) from either another REE (e.g., Er), group of REEs, or a non-REE, wherein there is no or substantially no other element, REE or non-REE, present after the separation (i.e., in the eluted solution). For example, preferential separation methods provided herein enable the separation of Nd (i.e., an individual REE) from Y, Pr, and Tb (i.e., groups of REEs) and/or from competing metals (i.e., non-REEs). In some embodiments, the preferential separation provides high purity separation of individual REEs, wherein there is no or substantially no other individual REE, group of REEs and/or non-REEs present after the separation (i.e., in the eluted solution).

In some embodiments, the REEs and/or groups of REEs are separated in a purity of at least about 10%, at least about 15%, at least about 20%, at least about 30%, at least about 40%, at least about 50%, at least about 55%, at least about 60%, at least about 65%, at least about 70%, at least about 80%, at least about 85%, at least about 90%, at least about 95%, or at least about 100%, relative to any other REE and/or group of REEs.

In some embodiments, the REEs and/or groups of REEs are separated in a purity of at least about 10%, at least about 15%, at least about 20%, at least about 30%, at least about 40%, at least about 50%, at least about 55%, at least about 60%, at least about 65%, at least about 70%, at least about 80%, at least about 85%, at least about 90%, at least about 95%, or at least about 100%, relative to any other element.

In some embodiments, the REEs and/or groups of REEs are separated in a purity of at least about 10%, at least about 15%, at least about 20%, at least about 30%, at least about 40%, at least about 50%, at least about 55%, at least about 60%, at least about 65%, at least about 70%, at least about 80%, at least about 85%, at least about 90%, at least about 95%, or at least about 100%, relative to any non-REE component.

In some embodiments, the methods provide preferential separation of REEs adjacent to each other on the periodic table. For example, in some embodiments, the methods provide preferential separation of La from Ce, Ce from Pr, Pr from Nd, Nd from Pm, Pm from Sm, Sm from Eu, Eu from Gd, Gb from Tb, Tb from Dy, Dy from Ho, Ho from Er, Er from Tm, Tm from Yb, and/or Yb from Lu.

In some embodiments, the methods provide preferential separation of REEs based on the ionic radius, atomic radius, and/or weight of the REE. In some embodiments, light REEs (LREEs) such as La, Cr, Pr, Nd, Sm, or Eu are preferentially separated from heavy REEs (HREEs) such as Gd, Tb, Dy, Ho, Er, Tm, Yb, Lu, Sm, or Y. In some embodiments, REEs with a smaller ionic radius are preferentially separated from REEs with a large atomic radius. For example, in some embodiments, $La^{3+}$ with an ionic radius of 103 pico meters (μm) is separated from $Lu^{3+}$ with an ionic radius of 86 μm. In some embodiments, the preferential separation of the REEs is influenced by the effects of the lanthanide contraction, wherein the ionic radii of the lanthanides significantly decrease upon moving from left to right on the periodic (i.e., La to Lu).

In some embodiments, methods of the present disclosure enable preferential separation of Tb from La, wherein the tunable solution comprises oxalate, citrate, EDTA, $NaHCO_3$, or any combination thereof. In some embodiments, the concentration of the tunable solution comprising oxalate, citrate, EDTA, $NaHCO_3$, or any combination thereof is varied between 0 mM to 35 mM or 0 mM to 120 mM. In another embodiment, the methods of the present disclosure enable preferential separation of Y, Pr, Tb, Ce, and La from Nd, wherein the tunable solution comprises oxalate and the concentration of the oxalate is varied between 0 mM to 120 mM. In yet another embodiment, the methods of the present disclosure enable preferential separation of Lu, Yb, Tm, Er, Ho, Y, Dy, Tb, Gd, Eu, Sm, Nd, Pr, Ce, and La, wherein the tunable solution comprises 1 mM or 2.5 mM of oxalate, wherein the concentration of the tunable solution is held constant throughout the separation. In another embodiment, the methods provide preferential separation of Pr, Nd, Tb, and Dy, wherein the tunable solution is oxalate and the concentration of the oxalate is varied between 0.1 mM to 100 mM.

In some embodiments, the microbes are added to a column prior to contacting the microbes encoding at least one REE binding ligand with the REE containing material. In some embodiments, prior to adding the microbes to the column, the microbes are formulated within or to the surface of a solid structure (e.g., a bead and/or capsule). When added to the column, the microbes are used, as defined conventionally in column chromatography, as the stationary phase. This enables a continuous flow system in which REE containing material is introduce to the column, and flows from the top to the bottom of the column.

In some embodiments, the present disclosure provides methods for preferentially separating REEs in a single step. Single step separation occurs when the REE-containing material is introduced to the microbes encoding at least one REE binding ligand once and results in the isolation and purification of the individual REE or groups of REEs with no or no or substantially no other element from a different group of REEs and/or non-REEs after the separation (i.e., the REE-containing material does not need to be introduced to the column more than once to achieve high purity). This contrasts conventional REE separation technologies that require multiple rounds of purification of the REE-containing material, which is not only inefficient, but also, expensive.

In some embodiments, the present disclosure provides methods for preferentially separating REEs by a selective desorption of REEs from the REE binding ligand. In some embodiments, the selective desorption is followed by a selective precipitation of the REE. In some embodiments, the REE precipitation step is a post-process step (i.e., occurs after the REEs are separated from the REE-binding ligands). Selective REE desorption and selective REE precipitation occurs when a specific REE (e.g., La) is targeted for desorption and precipitation without the desorption or precipitation of a different REE or non-REE. In some embodiments, the combination of the selective desorption of the REE from the REE binding ligand followed by the selective precipitation of the REE occurs by adjusting (i.e., varying the parameters) of the tunable solution. For example, in some embodiments, with a tunable solution at a pH of 6, the REEs are desorbed from the REE binding ligand and then, by adjusting the pH of the tunable solution to a pH of 1-2, the REEs are precipitated from the tunable solution. In some embodiments, the tunable solution that promotes the selective REE desorption and selective REE precipitation comprises oxalate, carbonate, or any combination thereof. In some embodiments, the selective desorption and selective adsorption occurs by varying the concentration, pH, temperature, pressure, or any combination thereof the tunable solution. By selectively desorbing and precipitating the REEs, REEs can be isolated with no or substantially no contamination from other REE and/or non-REEs. In some embodiments, the concentration, pH, temperature, and/or pressure of the tunable solution does not change. In some embodiments, when the tunable solution comprises an anionic component such as oxalate or carbonate, the REE is selectively precipitated as a complex of the anionic component (e.g. REE-oxalate complex or REE-carbonate complex). In some embodiments, the precipitated REE-anionic component complex can be separated from non-REE complexes (e.g., uranium complexes) that have also been selectively desorbed and selectively precipitated.

In some embodiments, the selective desorption and selective adsorption is facilitated by a tunable solution comprising more than one components, for example, 2, 3, 4, 5, or more components. The one or more components include oxalate, an inorganic acid, an organic acid, a carbonate salt, a buffer, an inorganic base, an organic base, a chelating agent or any combination as defined above. In some embodiments, the one or more components include oxalate, carbonate, EDTA, or citrate. In some embodiments, the tunable solution comprises oxalate and carbonate and selective desorbs and precipitates REE-oxalate complexes and REE-carbonate complexes. The use of a tunable solution comprising one or more components enables the preferential separation of the REE elements by selectively precipitating REEs. For example, carbonate may selectively precipitate one REE (e.g., La) while oxalate may selectively precipitate a different REE (e.g., Gd) as such the dual use of oxalate and carbonate facilitates the selective precipitation of the REEs.

In some embodiments, the REEs are adsorbed to and desorbed from the REE-binding ligand separately. For example, in some embodiments, upon contacting the microbes encoding at least one REE binding ligand with the REE-containing material, the REEs are adsorbed to the REE binding ligand (i.e., from a microbe-REE complex) and then upon introducing the tunable solution, the REEs are desorbed from the REE binding ligand (i.e., break apart the microbe-REE complex by dissociating the REE from the REE binding ligand). In some embodiments, the REE-containing material is flowed over a column comprising the microbes encoding at least one REE binding ligand until the column is saturated (i.e., all or substantially all REE binding ligands are bound to an REE or non-REE to form a microbe-REE). The initial adsorption step results in the majority (i.e., greater than 50%) of the non-REEs flowing through the column while the REEs are retained (i.e., bound by the REE binding ligand). The column is then washed with a neutral buffer to wash out unbound REEs or non-REEs. After saturation and wash, the tunable solution is used to differentially separate (i.e., elute) the REEs from the REE binding ligands.

In some embodiments, the REEs are adsorbed and desorbed from the REE binding ligand simultaneously during mass transport process. For example, in some embodiments, the REE-containing material is flowed over a column comprising the microbes encoding at least one REE binding ligand, wherein only a portion of the REE binding ligands adsorb an REE to from a microbe-REE complex. A tunable solution is then flowed through the column, wherein the REEs undergo a series of adsorption and desorption (i.e., is a dynamic process) from the REE binding ligand as REEs proceed from the top to the bottom of the column. The difference in affinity of each REE for the REE binding ligand (i.e., solid phase) and the tunable solution (i.e., mobile phase) controls the migration rate of the REEs through the column. By leveraging the effects of the lanthanide contraction, heavier REEs migrate faster than lighter REEs through the column, providing a means for the preferential separation of the REEs. The simultaneous adsorption and desorption process enables the separation of individual and/or groups of REEs in a high purity. This method provides advantages over conventional REE separation process which require the use of expensive chemical resins in order to obtain highly purified REEs and/or group of REEs.

In some embodiments, the methods for preferentially separating REEs from REE-containing material further comprise introducing a modified tunable solution. The modified tunable solution is a solution with a different concentration, pH, temperature, pressure, or a composition as compared to the tunable solution. The modified tunable solution preferentially separate REEs from the REE-containing material. The preferential separation can be achieved when the solution is modified in a manner in which the affinity of an individual or group of REEs for the solution (i.e., mobile phase) is increased while the affinity of the individual or groups of REEs for the REE binding ligands (i.e., stationary phase) is decreased. Conversely, the preferential separation can also be achieved when the solution is modified in a manner in which the affinity of an individual or groups of REEs for the REE binding ligand (i.e., stationary phase) is increased while the affinity of the individual or group of REEs for the REE solution is decreased.

In some embodiments, the methods for preferentially separating REEs are continuous and the REE separation is uninterrupted by additional energy-intensive steps such as centrifugation and/or filtration. In other embodiments, the methods for preferentially separating REEs comprise an additional step of centrifugation filtration, or both.

The REE-containing material may be any material known to contain or suspected to contain REE. In some embodiments the material is a solid material, a semi-solid material, or an aqueous medium. In a preferred embodiment, the material is an aqueous solution. Non-limiting examples of suitable materials for use in extraction of REE include rare earth ores (e.g., bastnasite, monazite, loparite, and the lateritic ion-adsorption clays), geothermal brines, coal, coal byproducts, mine tailings, phosphogypsum, acid leachate of solid source materials, REE solution extracted from solid materials through ion-exchange methods, or other ore materials, such as REE-containing clays, volcanic ash, organic materials, and any solids/liquids that react with igneous and sedimentary rocks.

In some embodiments, the REE-containing material is a low grade material wherein the REEs are present in less than about 2 wt % of the total weight of the low grade material. In other embodiments, the REE-containing material is a high grade material, wherein the REE are present in greater than about 2 wt % of the total weight of the high grade material.

In some embodiments, the REE-containing material comprises less than about 5 wt %, less than about 10 wt %, less than about 15 wt %, less than about 20 wt %, less than about 25 wt %, less than about 30 wt %, less than about 35 wt %, less than about 40 wt %, less than about 45 wt %, less than about 50 wt % REEs of the total weight of the REE-containing material.

The microbes can also be used for recovering REE from recycled REE-containing products such as, compact fluorescent light bulbs, electroceramics, fuel cell electrodes, NiMH batteries, permanent magnets, catalytic converters, camera and telescope lenses, carbon lighting applications, computer hard drives, wind turbines, hybrid cars, x-ray and magnetic image systems, television screens, computer screens, fluid cracking catalysts, phosphor-powder from recycled lamps, and the like. These materials are characterized as containing amounts of REE, including, for example, scandium, yttrium, lanthanum, cerium, praseodymium, neodymium, samarium, promethium, europium, gadolinium, terbium, dysprosium, erbium, thulium, ytterbium, lutetium, or any combination thereof.

In some embodiments, the material is pre-processed prior to providing the microbes. Non-limiting examples of suitable pre-processing includes acid leaching, bioleaching, ion-exchange extraction, pH adjustment, iron oxide precipitation, temperature cooling (e.g., geothermal brines). In other embodiments, prior to providing the microbes, the REE-containing material is refined to remove at least a portion of non-REE metals. In some embodiments, the non-REE metals are extracted using microbes, for example, genetically modified or unmodified *C. crescentus.*

In some embodiments, at least a portion of the microbes are attached (i.e., immobilized) to a surface of a solid support prior to contacting with a REE-containing material. It is contemplated that microbe immobilization in biosorption medium for use in flow-through setups allows for complete (or substantially complete) separation of REEs from REE-containing mixed metal solutions in a single step. In one embodiment, about 20%, about 30%, about 40%, about 50%, about 60%, about 70%, about 80%, about 90%, about 91%, about 95%, about 97%, about 98%, about 99%, or 100% of the REE in the REE-containing material (e.g., mixed metal solution) is extracted in a single step. In some embodiments, about 1%, 5%, 10%, 15%, 20%, about 30%, about 40%, about 50%, about 60%, about 70%, about 80%, about 90%, about 91%, about 95%, about 97%, about 98%, about 99%, or 100% more of the REE in the REE-containing material (e.g., mixed metal solution) is extracted in a single step as compared to an amount of REE extracted in a single step using conventional extraction methods.

The binding of REE to the microbes can be reversible. In some embodiments, at least a portion of the REE in the microbe-REE complex is desorbed (i.e., removed or separated) from the microbes. Non-limiting examples of suitable methods include acid treatment (e.g., sulfuric acid/$HNO_3$ and HCl), citrate, acetate, and gluconate. In a preferred embodiment, the removal step is performed by acid-stripping. In another preferred embodiment, wherein the removal step is performed using an amount of citrate.

The microbes can also be reused. In some embodiments, the methods further comprise removing the REE from the microbes to regenerate microbes. The microbes can be used 2, 3, 4, 5, 6, 7, 8, 9, 10, 15, 20, 25, 30, or more times. In other embodiments, the microbes are single use. The microbes can be re-conditioned by any means known to one of skill in the art. For example, the microbes may be cleaned with buffer to wash off the citrate to re-generate microbes. In one embodiment, the methods further comprise reusing the regenerated microbes to carry out the extraction of REE from REE-containing material.

The microbes can be reused 2, 3, 4, 5, 6, 7, 8, 9, 10, 15, 20, 25, 30 or more times while also maintaining their high adsorption capacity. In some embodiments, the microbes maintain an adsorption capacity of about 1.0 mg of REE, about 1.5 mg of REE, about 2.0 mg of REE, about 2.5 mg of REE per g of the microbes during each of the adsorption cycles. In some embodiments, the microbes maintain an adsorption capacity of 1.5 mg of REE per g of the microbes for 9 cycles.

Aspects of the disclosure provide a kit of parts comprising: (a) genetically engineered microbes comprises an (a) genetically engineered microbes comprising an exogenous nucleic acid sequence encoding at least one REE binding ligand; (b) a tunable solution; and (c) instructions for differentially separating REEs from a REE-containing material.

EXAMPLES

Example 1: Biofilm-Based Continuous Flow Through System for REE Recovery

To enable industrial application of the REE-adsorbing microbes in an economical and scalable manner, a biofilm-based continuous flow through system for REE recovery in an airlift bioreactor will be developed. Further, moving beyond REE recovery, this system will also address the more challenging problem-separation among REEs. In addition to column chromatograph based on biosorption, a new mechanism of microbe-facilitated REE mineralization will be explored. The remarkable preference for heavier REEs during the biomineralization can provide a novel and effective approach for REE separation. In addition to REEs, the critical material palette will be expanded to include Scandium (Sc), Gallium (Ga) and Indium (In).

It is contemplated that this system will enable cost-effective REE recovery from low grade feedstock. The high abundance of some non-traditional REE resources offers an attractive alternative for obtaining REEs. However, no technology currently exists to cost-effectively extract REEs from them. As such, this system will focus on the development of a novel biosorption-based REE recovery process that can enrich and concentrate REEs from various low-grade feedstock, providing REE concentrate intermediate that can be readily used by other REE purification processes. The result will enable a mineral processing engineering design for REE extraction that is robust, easy to trouble shoot, and can be readily scaled up and adopted by industry.

This technology will also provide a new process for REE separation that does not involve solvents. In contrast, current techniques used in REE separation involve many stages of solvent extraction, which is expensive and harmful to the environment. As such, novel methods for REE separation that are potentially economical and ecofriendly will be explored. Initial efforts will focus on separating the 17 REEs into to a few (several) groups, followed by focusing on separating neighboring REEs.

The development of new technologies that enable recovery of REEs from low-grade feedstocks will also improve the economics of existing operations/waste streams, while diversifying the availability of critical material resources in the U.S. The successful execution of this study will revolutionize waste-to-product conversions and offer a promising opportunity of REE recovery in an economically viable and ecofriendly manner.

Scalability is also an important characterization for consideration in the development of a system for REE recovery. A critical step in scaling up the biosorption technology is the development of a continuous flow system using immobilized cells, allowing complete separation of REE ions from the aqueous solution in a single step, without the need of energy intensive step of centrifugation or filtration for the separation of microbes.

In addition to scalability, rare earth loading capacity is a crucial consideration in the development of a system for REE recovery. To improve on REE loading relative to biomass, a biofilm matrix material, curli, for the display of LBTs will be utilized. A new mechanism of recovery will also be used—biomineralization, defined as metabolically accelerated crystal growth to distinguish this type from the less extensive biosorption. Compared to biosorption, biomineralization can induce very high loadings without saturation constraints, controlled by biochemical and chemical processes occurring at the cell surface.

REE recovery based on biosorption by LBTs has low separation power (less than 2-3 fold) among individual REEs. To improve on REE separation, two additional strategies will be employed: one is to include a column chromatography with a flexible mobile phase, and the other is a REE-specific mineralization step.

Rare Earth Biosorption by Multi-Functional Biofilms in a Flow-Through Process

An important consideration for the biosorption process design is cell immobilization-enabled flow-through operation. Cell immobilization allows easy separation of the feed solution and REEs that are attached to the cell surface, allowing continuous operation without the need of energy-intensive centrifugation or filtration. To this end, multi-functionalized biofilms for REE adsorption in a flow-through system will be built.

Figure 1B:
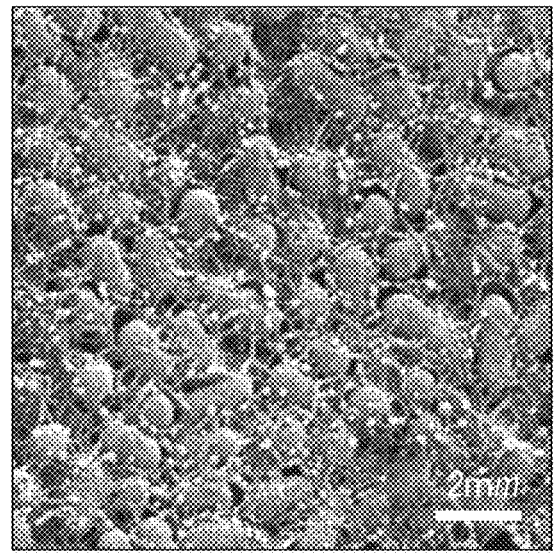
Figure 1C:
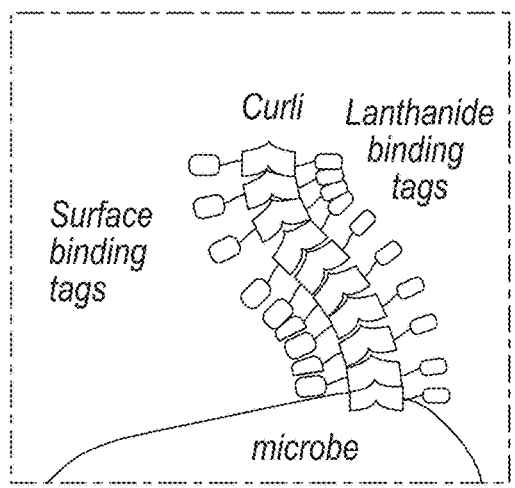
FIGS. 1C and 1D are representative schematics of surface binding peptides bound to a biofilm.
Figure 1D:
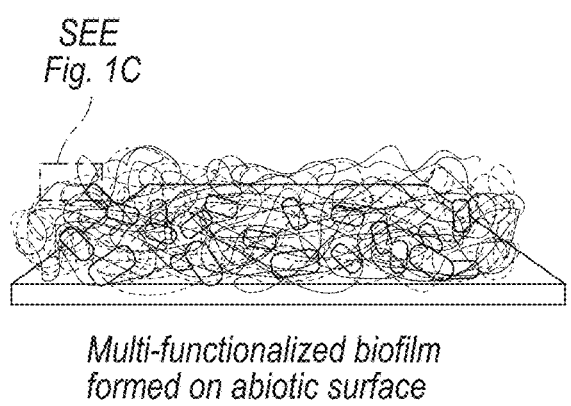

To improve on the surface adhesion properties of *E. coli* biofilm matrix, it is critical to tune the nanofiber adhesion to specific abiotic surfaces. To achieve this, various surface binding peptides (e.g., glass, steel and carbon nanotubes) will be attached to extracellular curli. Curli are the extracellular adhesive amyloid fibers that serve as an adhesive and structural scaffold to promote biofilm assembly. FIGS. 1A and 1B are scanning electron microscopy images of non-curli and curli producing strains of *E. coli*, respectively. As surface binding peptides, curli can impart adhesive function to biofilms that can withstand very rigorous washing conditions. To further improve on the REE adsorption capacity of biofilm and develop more effective biological interfacial materials, additional lanthanide binding tags (LBT) will be appended on the curli as shown in the schematic in FIGS. 1C and 1D. Specifically, FIGS. 1C and 1D shows biofilms that are functionalized with both lanthanide binding tags and surface binding tags, which can be used for REE recovery in a flow-through system. Molecular programming of the bacterial extracellular matrix material (curli) by genetically appending the surface binding tags and lanthanide binding tags (LBTs) using the recently developed Biofilm-Integrated Nanofiber Display (BIND) technology will be conducted. Importantly, by combing the programmed biofilm adhesion and LBT-display on the biofilm matrix and cell surface, it is contemplated that the engineered multi-functional biofilm will be as ideal as a chemical processing platform for REE recovery. Multi-functional biofilms that are capable of adhering to plastic biofilm carriers will be tested for REE recovery in an airlift bioreactor.

Rare Earth Biosorption in an Airlift Bioreactor

Figure 2:
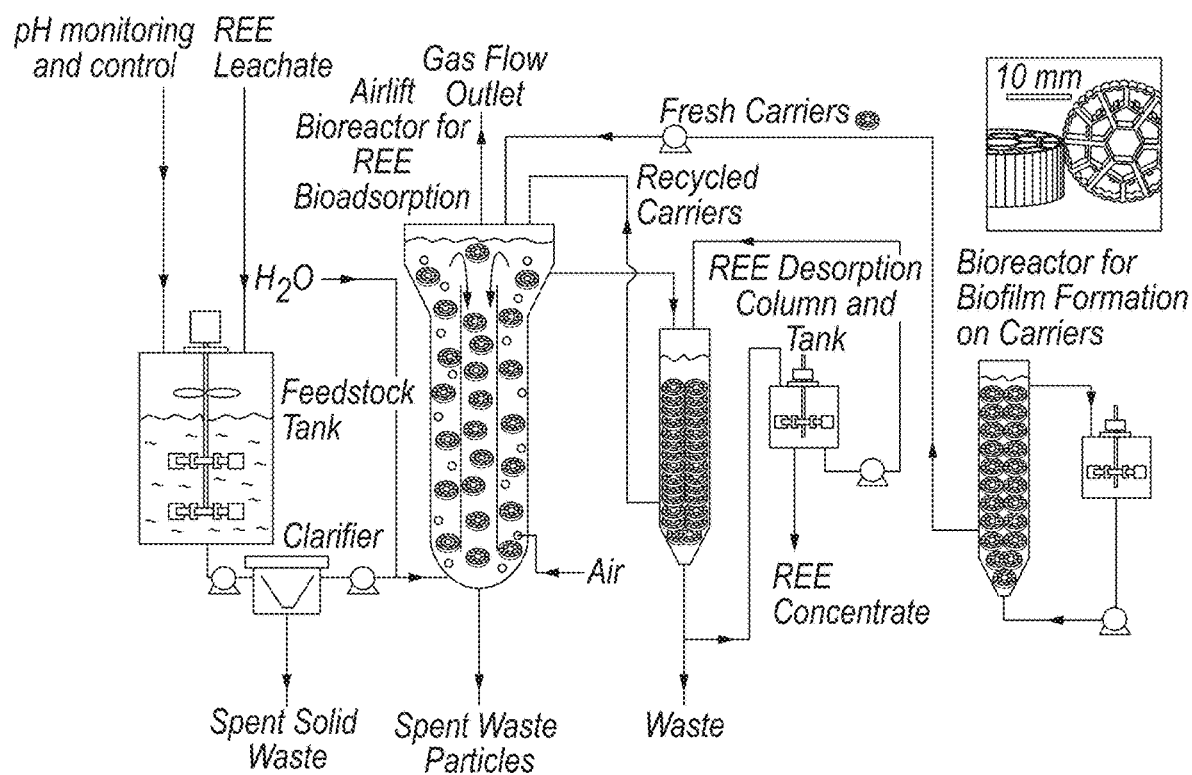
FIG. 2 is a representative schematic of an airlift bioreactor for REE biosorption according to an embodiment of the disclosure.

An airlift bioreactor was designed for REE biosorption as shown in FIG. 2. FIG. 2 depicts an example airlift bioreactor design and flow diagram where the proposed system consists of a two-stage semi-continuous process. The process includes (1) a closed mechanically agitated bioreactor (MAB) used to grow the microbes, (2) an open cylindrical container as a packed column for biofilm formation on carrier disks, (3) an airlift bioreactor for adsorption of REE onto biofilm carrier disks, (4) an open-packed elution column with (5) circulating citrate from a citrate tank for REE desorption and recovery. This reactor builds upon long-standing biosorption technology that has been well-recognized in industrial-scale applications for biomining and bioremediation. The reactor also offers low shear force with high mixing to minimize potential biofilm damage and increases REE biosorption efficiency. In this study, a bench-scale air-lift bioreactor as shown in FIG. 2 will be built and performance tested to assess its potential to be developed, economically into an industrial-scale production system.

Cell Encapsulation and Column Chromatography for REE Separation

Column chromatography made of biomaterial-polymer beads will be used for separating individual REEs. The development of the new efficient chelating exchange resin will work similarly to the traditional ion chromatography, but at a fraction of the cost. This platform couples the high capacity and selectivity of biomaterials with high surface area to facilitate rapid and controlled biosorption and desorption of REEs. All types of biomaterials available including whole cells of *Caulobacter* and *E. coli*, shed LBT-tagged curli and S-layer will be tested. There will be a focus on optimizing polymer material, bead size, and biomass loading.

REE separation is primarily based upon the exploitation of REE complexation properties. Depending on the stationary and the mobile phases used, different mechanisms govern REE retention. Given the high selectivity of the REE-adsorbing microbes, it is contemplated that the encapsulated biomaterials will have high resolution to enable the separation of individual REEs. Behavior for the series of 14 REEs separated as anionic complexes, with different ligands (e.g., bicarbonate, EDTA, citrate, oxalic acid and bicarbonate) used as the mobile phase will be examined. In combination with gradient elution and optimization of other parameters (e.g., column length and flow rate), it is contemplated that this system for REE recovery will achieve effective separation of individual REEs.

Figure 3D:
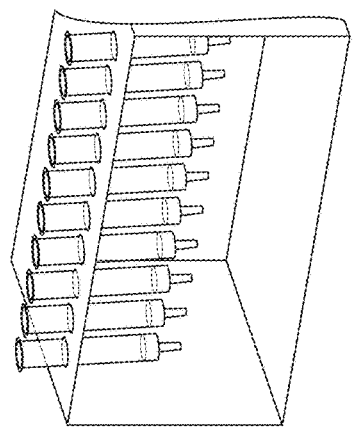
FIG. 3D depicts a representative flow-through setup according to an embodiment of the disclosure.
Figure 3F:
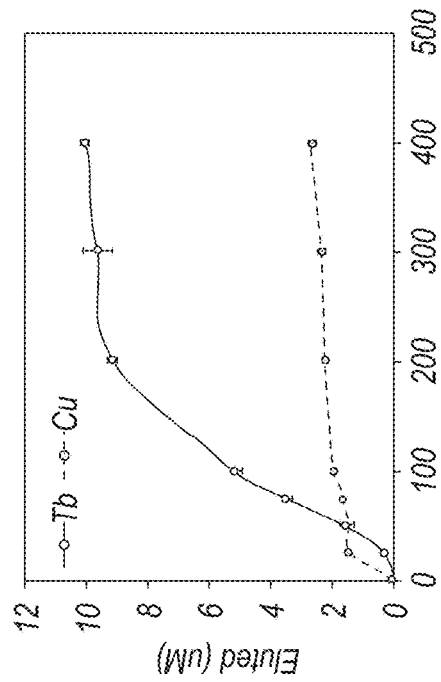
FIGS. 3E-3G are representative plots of the separation of REE according to an embodiment of the disclosure.
Figure 3E:
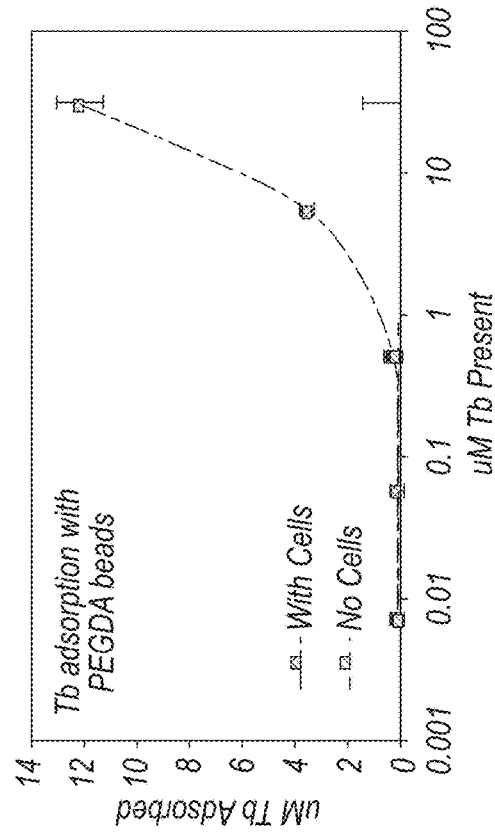
Figure 3G:
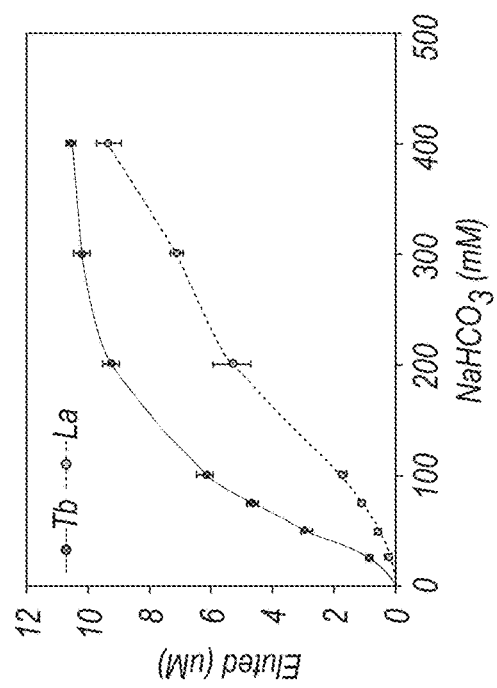

FIGS. 3A-3C depict an example embodiment of the column chromatography for REE separation with polymer beads under follow-through. FIGS. 3A and 3B are conceptual illustrations of the polymer bead, FIG. 3C is a corresponding SEM image of the PEDGA beads and FIG. 3D is an example set up of the flow-through system with the PEDGA beads. Importantly, this system enables the absorption of REEs as depicted in FIGS. 3E-3G, wherein a column experiment with the PEDGA beads demonstrated that PEDGA has no background REE adsorption whereas beads with embedded cells show a good absorption efficiency. This column chromatography setup also showed through competition experiments that when an equal amount of Tb/Copper (Cu) are Tb/La were absorbed onto the REE-absorbing *E. coli*, there was a preferred desorption of Tb over Cu, and Tb over La. As such, the column chromatography for REE separation provides a promising platform by which individual REEs can be separated.

REE Recovery and Separation Through Biomineralization of Rare Earth Hydroxides

Compared to biosorption, biomineralization can induce very high metal loadings without saturation constraints, controlled by biochemical and chemical processes occurring at the cell surface. As defined herein, biomineralization is metabolically accelerated crystal growth to distinguish this type from the less extensive biosorption mechanism. Recent discovery of synthetic peptides, lanthanide mineralization tags (LMT), enable the formation and precipitation of rare earth hydroxides under circumneutral pH, condition precipitation otherwise does not occur. However, high concentrations of both peptides and the REEs were required for the biomineralization to occur.

To circumvent the requirement of high REEs and peptide concentrations, this system for REE recovery will display lanthanide mineralization ligands on cell surface through S-layer, OmpA and/or curli. Thus, both peptides and REEs are expected to be present at high concentrations locally, in juxtaposition of cell wall components that may function as foci for the onset of rare earth precipitation. As such, rare earth precipitation at the cell surface is promoted; rare earth precipitated can be removed and recovered from the solution if the cells are immobilized in a flow-through system or other continuous filtration process is developed.

REE Recovery by Biomineralization of Rare Earth Phosphate

Figures 4A, 4B, 4C:
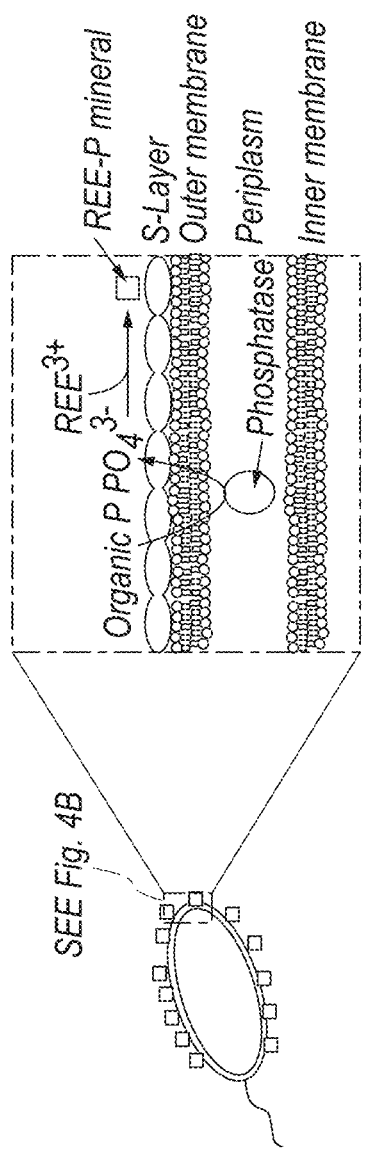
FIGS. 4A and 4B depict a representative model for REE biomineralization according to an embodiment of the disclosure.
FIG. 4C is a representative tunneling electron microscopy (TEM) image of a biomineralization precipitate according to an embodiment of the disclosure.

As shown in FIGS. 4A and 4B, *Caulobacter* can facilitate biomineralization of uranium (U) phosphate on the cells surface via its native alkaline phosphatase activity. Specifically, FIGS. 4A and 4B depict a conceptual model for rare earth biomineralization where a phosphate in the periplasmic space, catalyzes rare earth biomineralization by cleaving organic phosphate to produce inorganic phosphate. The inorganic phosphate then precipitates on with the rare earth ions to produce rare earth-phosphate precipitates on the cell surface. FIG. 4C is a TEM image depicting U phosphate precipitates on the cell surface via biomineralization. Due to the similarity of uranium and rare earth in phosphate complexation and precipitation, it is contemplated that *Caulobacter* might also catalyze biomineralization of rare earth phosphate, as well as americium phosphate.

To exploit the biomineralization activity for REE recovery, alkaline or acid phosphatase will be overexpressed to promote the formation and precipitation of rare earth phosphate on the cell surface. The local production of the phosphate as well as the component of the cell surface will likely serve as a nucleation site for initial rare earth deposition and precipitation to occur. By controlling the amount and rate of organic phosphate supply, it is contemplated that this process will promote selective rare earth precipitation and recovery. The task will define and characterize biogenic rare earth minerals during biomineralization and demonstrate its potential utility in REE recovery.

Example 2: Bio-Based Material for Rare Earth Element Separation

Liquid-liquid extraction and ion exchange are the predominate technologies for REE separation and purification. However, both techniques are limited in terms of their environmental impact as well as associated cost. To overcome the technical, economic, and environmental limitations of current REE separation approaches, the following example describes an alternative, bio-based material for REE separation. It is contemplated that the bio-based material for REE separation will enable a low-cost recovery and separation process that is broadly applicable to both high and low-grade REE feedstocks.

Figure 5A:
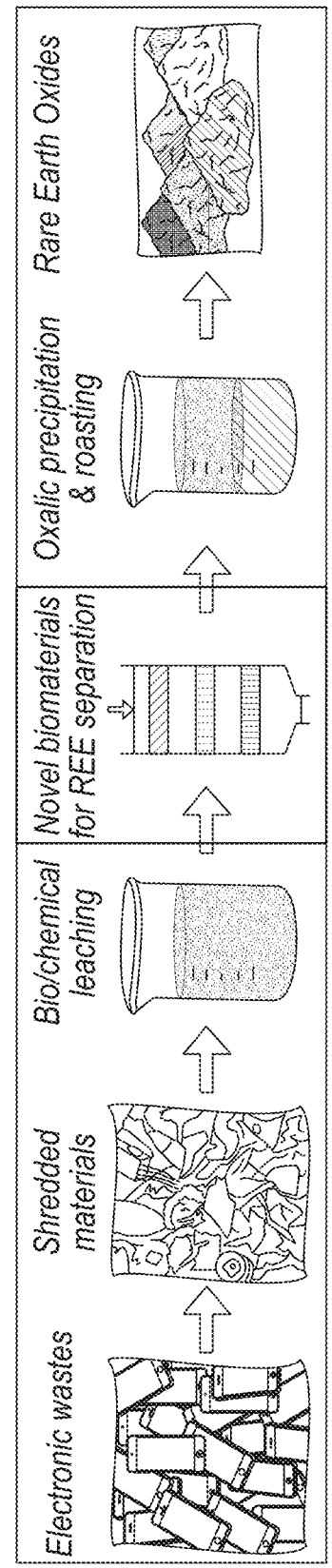
FIG. 5A is a representative schematic of the process of REE separation according to an embodiment of the disclosure.
Figure 6A:
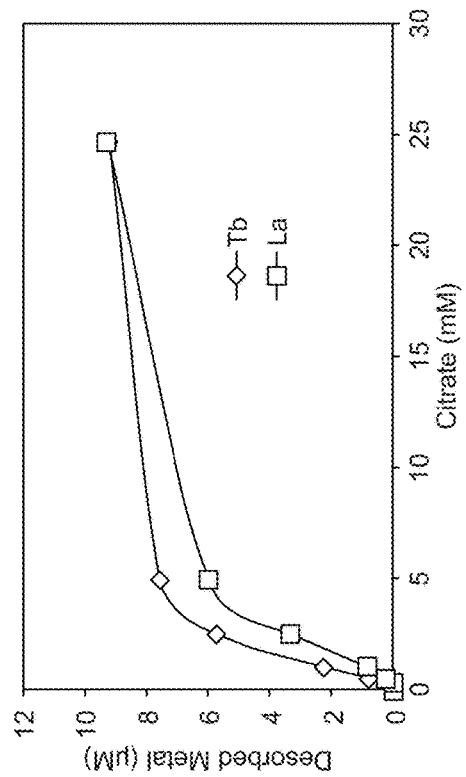
FIGS. 6A-6D are representative plots of the preferential desorption of terbium (Tb) and lanthanum (La) using the select eluents, oxalate and sodium bicarbonate, according to an embodiment of the disclosure. The plots demonstrate that by tuning the concentration of the oxalate and sodium bicarbonate in the tunable solution heavy vs light REEs can be preferentially desorbed.
Figure 6B:
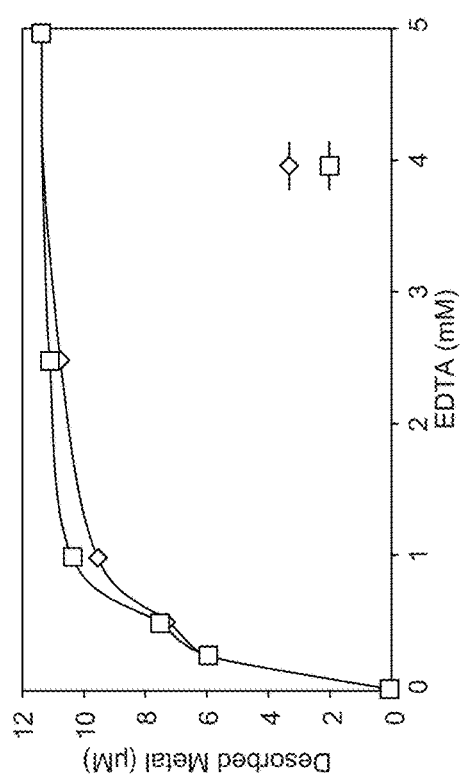
Figure 6C:
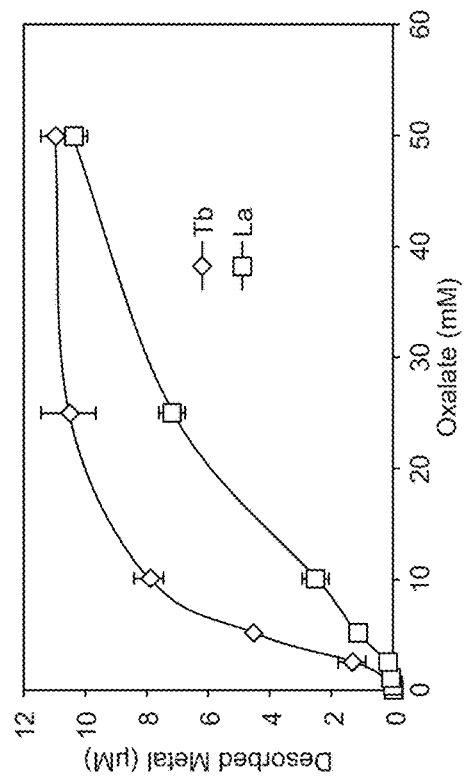
Figure 6D:
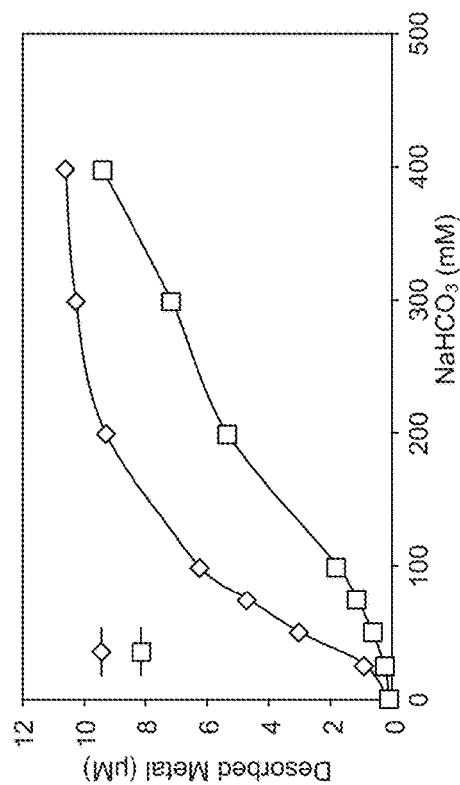
Figure 7A:
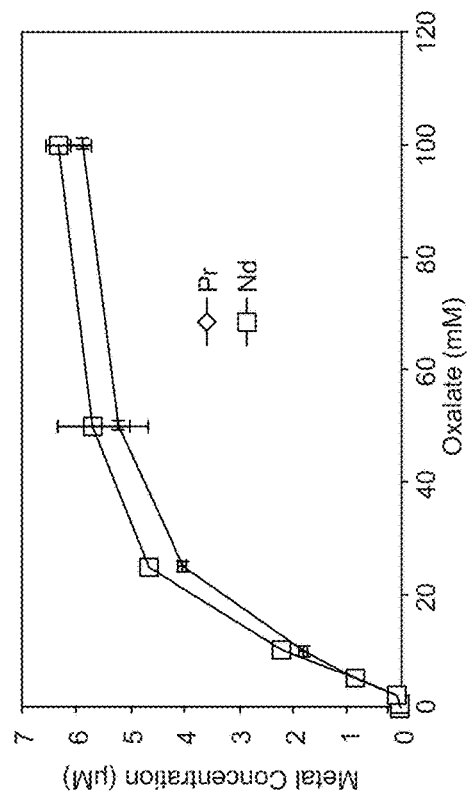
FIGS. 7A-7E are representative plots of the preferential desorption of pairs REEs according to an embodiment of the disclosure. The plots demonstrate that using oxalate as an eluent, REE pairs can be preferentially desorbed.
Figure 7B:
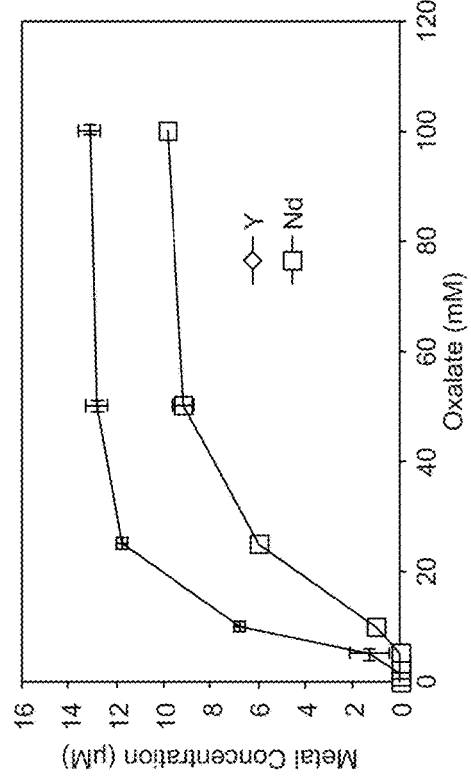
Figure 7C:
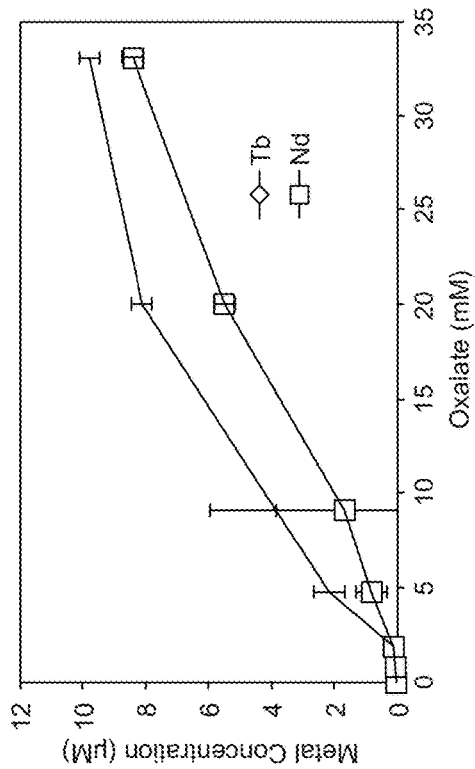
Figure 7E:
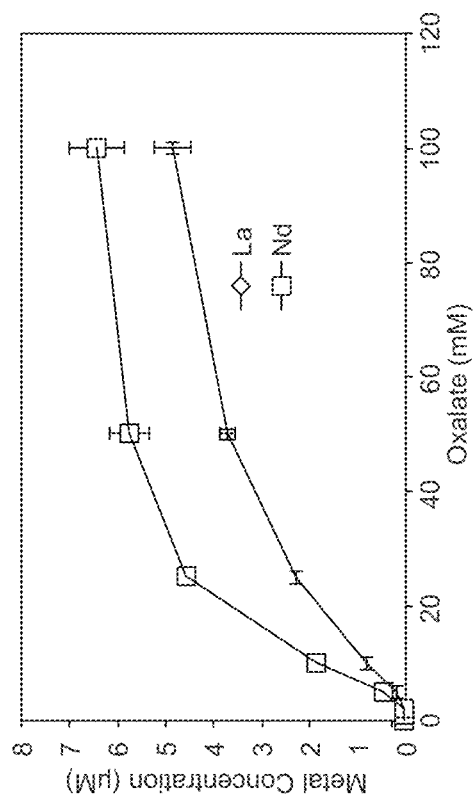
Figure 7D:
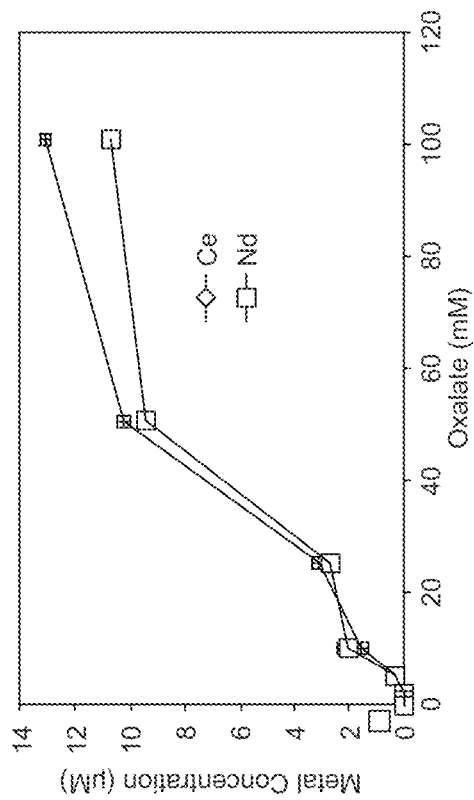

The bio-based material consists of LBT-displayed *E. coli* and/or *C. crescentus* cells embedded within a polymer matrix (e.g., PEDGA) and used as a column chromatography resin that enables a continuous flow system for the separation of individual REEs from aqueous REE-containing feedstocks. FIGS. 5A-5D depict an example implementation of the REE separation system in which a micro-based resin material is used in column chromatography to separate individuals REEs based on their differential elution behavior. As shown in the schematic in FIG. 5A, the process of REE separation can be couple with upstream and downstream processes to produce individual rare earth oxides. FIG. 5B further provides a schematic in which the bioengineered microbes REE-absorbing microbes are embedded into a hydrogel (e.g., PEGDA) to make microbe beads for use as the stationary phase for REE separation. Further, FIGS. 5C and 5D are SEM and confocal microscopic images of the embedded, bioengineered microbe beads, respectively.

In a primary embodiment of the REE separation system as depicted in FIGS. 5A-5D, REE separation will be achieved by exploiting differences in REE complexation preferences between LBT-displayed biomaterials (stationary phase) and anionic eluents (mobile phase). Specifically, the REE-bearing solution (e.g., a solid feedstock leachate or a geothermal brine) is added to the column containing a packed bed of microbe beads. Subsequently, an eluent (e.g., oxalate, bicarbonate, or HCl) at a concentration that is predetermined based on batch-scale analysis, is then passed through the column. The rate at which individual REEs migrate through the column will be a function of their affinity for both the mobile and stationary phases. Although the REEs exhibit extremely similar chemical properties, they can be separated in an ion exchange column due to lanthanide contraction. Moving from left to right on the periodic table, the ionic radii of the lanthanides get smaller and therefore the stability of the REE complexes increases. This trend can be exploited with a properly designed ion exchange column to separate the individual rare earth metals from each other.

The batch-scale data as shown in FIGS. 6A-6D provide a proof-of-principle for REE separation in the column chromatography setup. The separation power of several different anionic eluents (e.g., bicarbonate, EDTA, citrate, oxalic acid) and pH was determined. Using a range of concentrations of each eluent to desorb REE pairs from LBT-displayed cells, oxalate and bicarbonate, both medium strength complexants of REEs, exhibited preferential desorption of Tb over La and offered the greatest promise for REE separation. Importantly, these data indicate that concentration of oxalate and sodium bicarbonate can be fine-tuned for preferential desorption of heavy vs light REEs from the cell surface in batch experiments. Subsequent analysis revealed that oxalate also enabled differential desorption with other REE pairs of relevance to REE-feedstocks (E-waste, ores, and coal combustion products) from the engineered *E. coli* cell surface, including Tb/Nd, Y/Nd, and La/Nd as shown in FIGS. 7A-7E.

Figure 8:
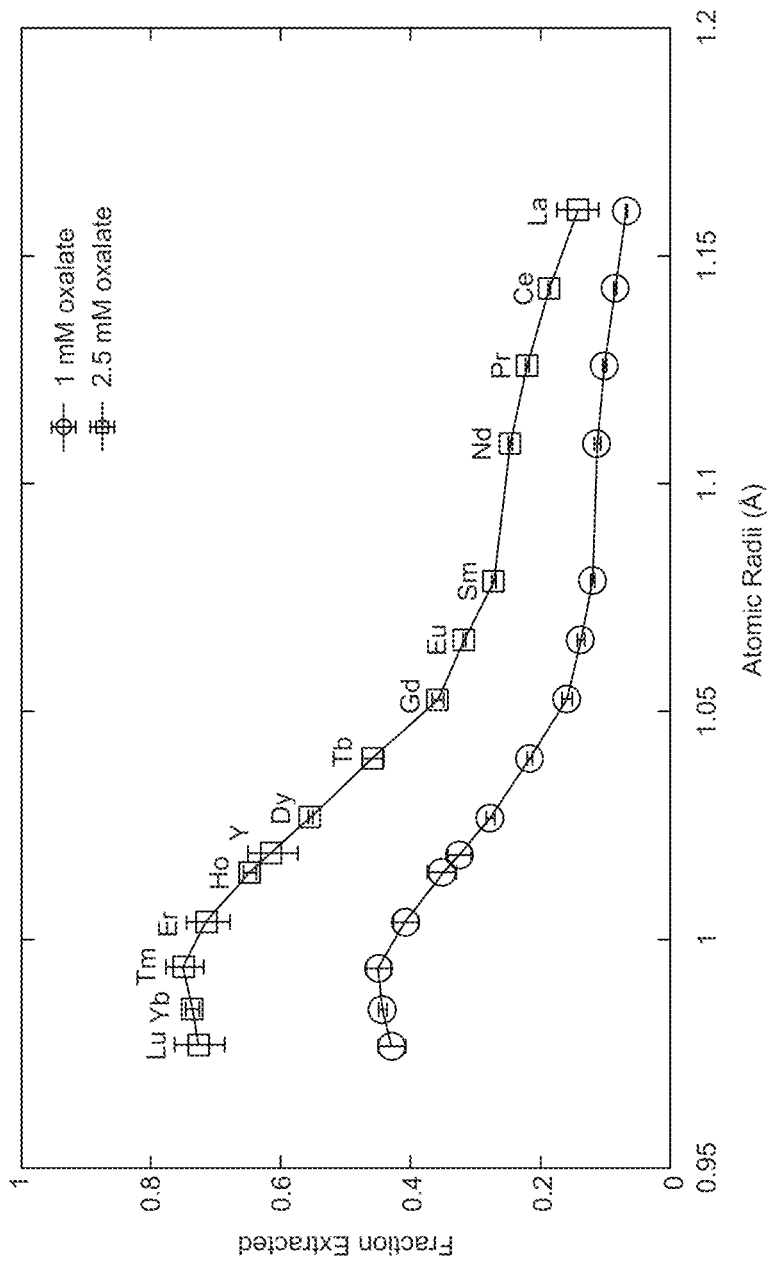
FIG. 8 is a representative plot of the separation of REEs based on weight using the eluent oxalate according to an embodiment of the disclosure. The plot demonstrates that using oxalate as and eluent and without varying the concentration of the oxalate, REEs adjacent to each other on the periodic table can be preferentially separated.
Figure 10:
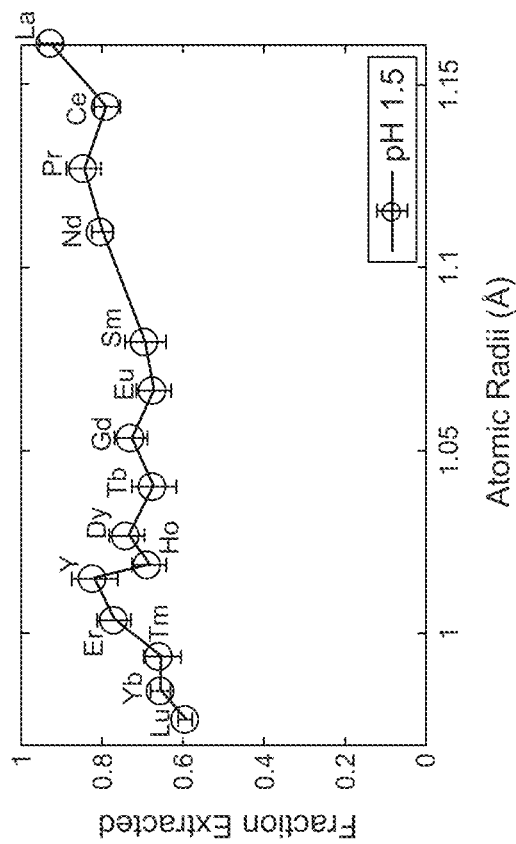
FIG. 10 is a representative plot of the separation of REEs based on weight using the eluent hydrochloric acid (HCl) solution with a pH of 1.5 according to an embodiment of the disclosure.
Figure 9:
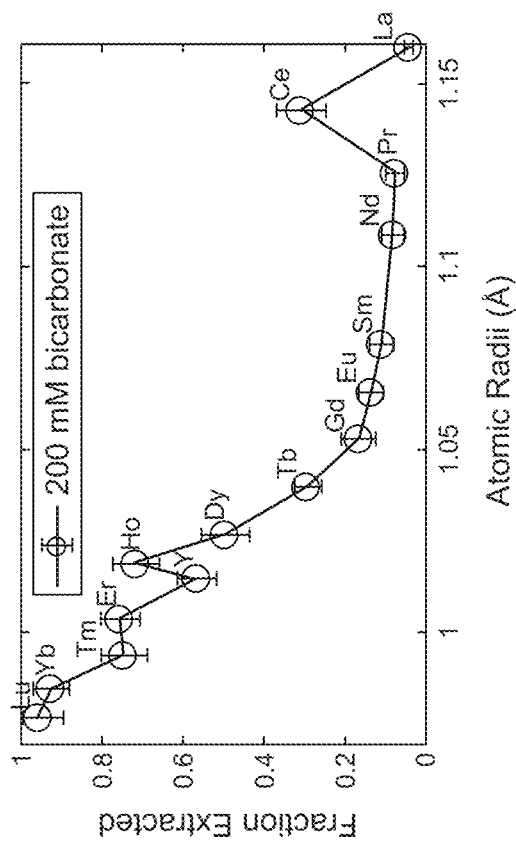
FIG. 9 is a representative plot of the separation of REEs based on weight using the eluent bicarbonate according to an embodiment of the disclosure. The plot demonstrates that using bicarbonate as an eluent and without varying the concentration of the bicarbonate, REEs adjacent to each other on the periodic table can be preferentially separated.

Additionally, oxalate desorption experiments with the entire lanthanide series revealed a strong desorption preference for heavy REEs over light REEs as shown in FIG. 8. In this experiment, equimolar concentrations of 15 REEs were adsorbed to the cell surface and desorbed with either 1 or 2.5 mM oxalate. At 2.5 mM oxalate, FIG. 8 depicts exemplary differential REE desorption behavior for light vs heavy REEs and for adjacent REEs from Nd to Er. Unexpectedly, a significant difference in the desorption preference was observed for adjacent REE pairs from Nd/Sm to Ho/Er, supporting the viability of separating adjacent REEs. A similar desorption profile was observed using bicarbonate as shown in FIG. 9. Specifically, FIG. 9 demonstrates that equimolar concentrations of 15 REEs were adsorbed to the cell surface and desorbed with 200 mM bicarbonate. Further, as shown in FIG. 10 equimolar concentrations of 15 REEs were adsorbed to the cell surface and desorbed with a 32 mM of HCl at a low pH of 1.5.

Figures 11A, 11B:
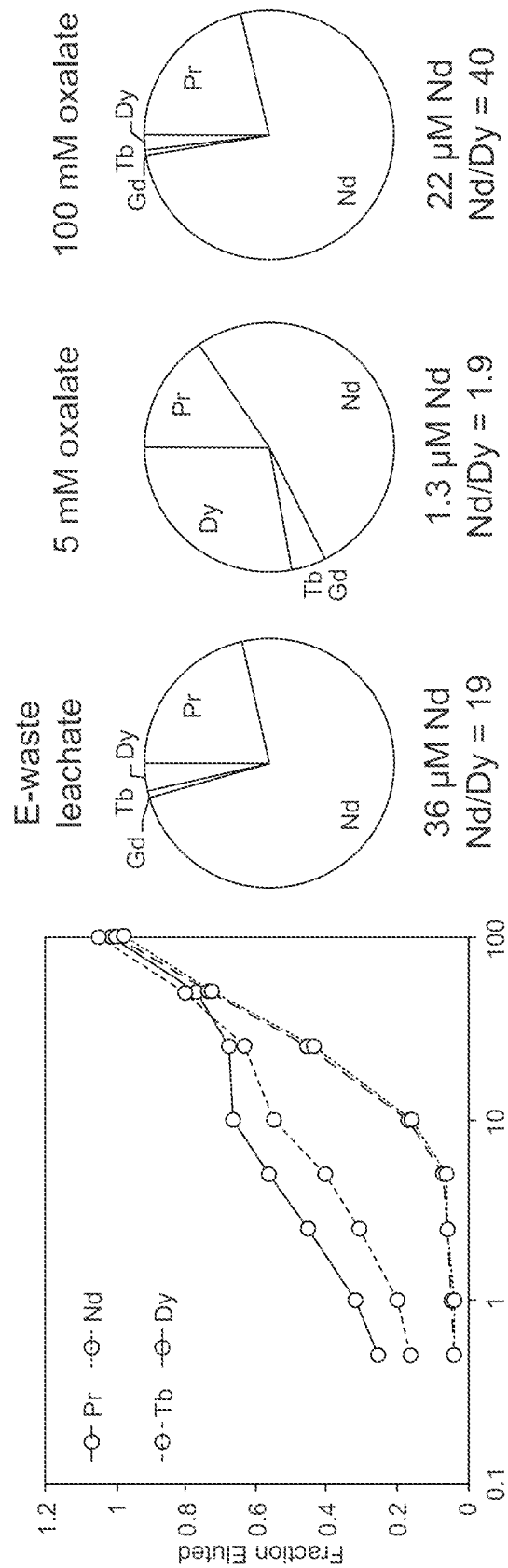
FIG. 11A is a representative plot of the separation of REEs from leachate of electronic waste.
FIG. 11B shows representative pie graphs for the corresponding quantity of REEs according to the separation in FIG. 11A according to an embodiment of the disclosure.

These data further suggest that this proof-of-concept differential desorption is applicable to industrially relevant feedstocks. For example, coupling biosorption of electronic waste leachates in batch with an oxalate-mediated desorption scheme enables partial separation of Dy/Tb from Nd/Pr as shown in FIGS. 11A and 11B, a result that can be further improved in a column chromatography setup.

In sum, through systematic characterization of the adsorption/desorption process with LBT-displayed cells, this study demonstrates that the anionic eluent (e.g., oxalate and bicarbonate) concentrations can be tuned to facilitate the differential desorption of REEs from the cell surface. This technology leverages these innate desorption preferences over the length of a column packed with microbeads, enabling the separation of individual REEs. Importantly, it is contemplated that this low-cost recovery process will be broadly applicable to a wide range of metal-containing feedstocks for a large palette of critical metals.

Microcapsule Synthesis and Column Performance

A critical step in scaling up the biosorption technology is the development of a continuous flow system that facilitates the separation of REE/microbes from the bulk solution in a single step without the need for the energy intensive step of centrifugation or filtration. To accomplish this, a scalable, inexpensive, bulk emulsion method for embedding microbes within PEGDA beads (i.e., microbe beads) was developed. PEGDA was utilized as the encapsulation matrix due its biocompatibility, high porosity, and hydrophilic properties. Initial efforts using a microfluidic platform yielded unsatisfactory cell loading due to clogging of the microfluidic capillaries. To improve cell loading, an emulsion method was utilized. Briefly, a high-density cell suspension, PEGDA, Ethyl (2,4,6-trimethylbenzoyl) phenylphosphinate (TPO-L) photoinitiator, and polydimethylsiloxane (PDMS) oil were emulsified by vigorous shaking and the resulting microdroplets were polymerized using UV light. This method enabled a high cell loading density and REE adsorption capacity, and enabled bead synthesis in higher throughput, albeit with lesser control over the size of the beads. Capsule stability was tested and the beads were stable for over 3 months under storage conditions (4° C.).

Figure 12A:
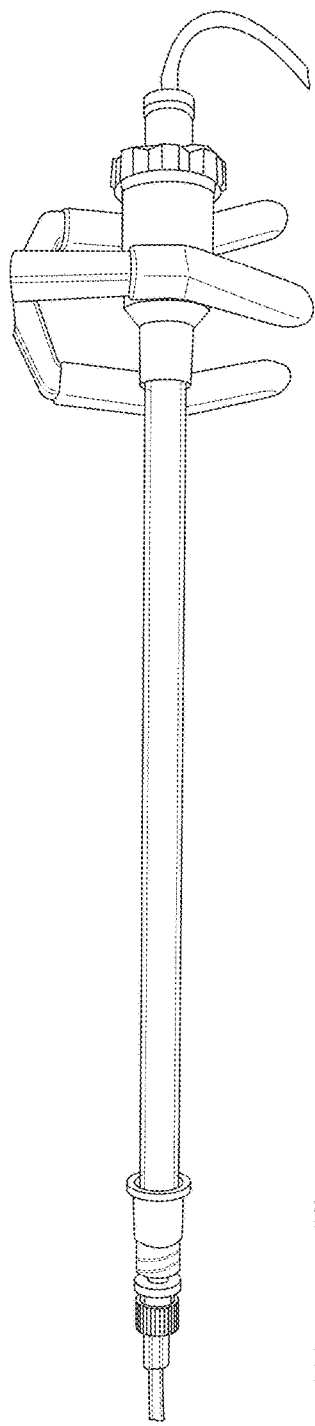
FIG. 12A is a representative flow through column setup for the separation of REEs according to an embodiment of the disclosure.
Figure 12B:
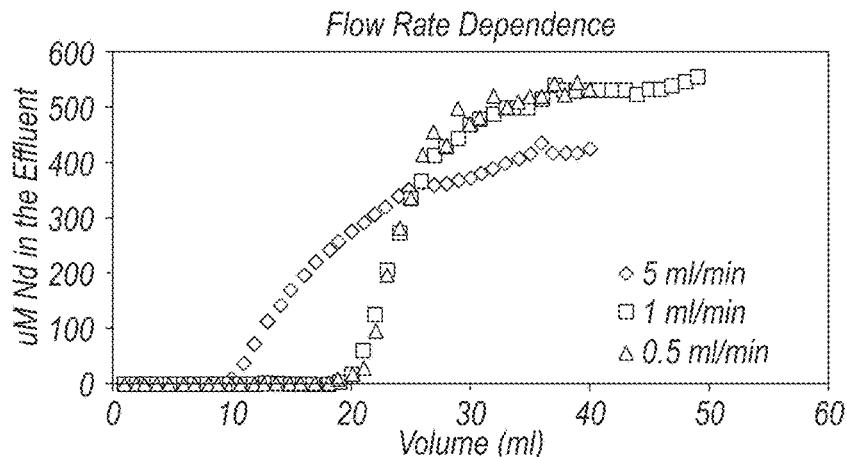
FIG. 12B is a representative plot of the rate dependence on the separation of neodymium (Nd) according to an embodiment of the disclosure. The plot demonstrates that the breakthrough (i.e., threshold in which REE in the effluent concentration matches the influent concentration) is unaffected up to a flow rate of 1 mL/min.
Figure 12C:
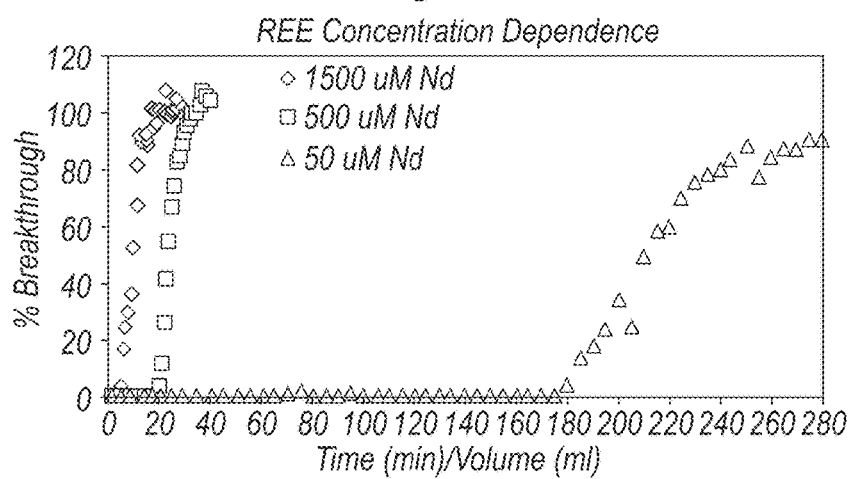
FIG. 12C is a representative plot of the concentration dependence on the separation of Nd according to an embodiment of the disclosure. The plot demonstrates that the adsorption kinetics of the REEs from the microbes is unlikely to limit the column performance.
Figure 12D:
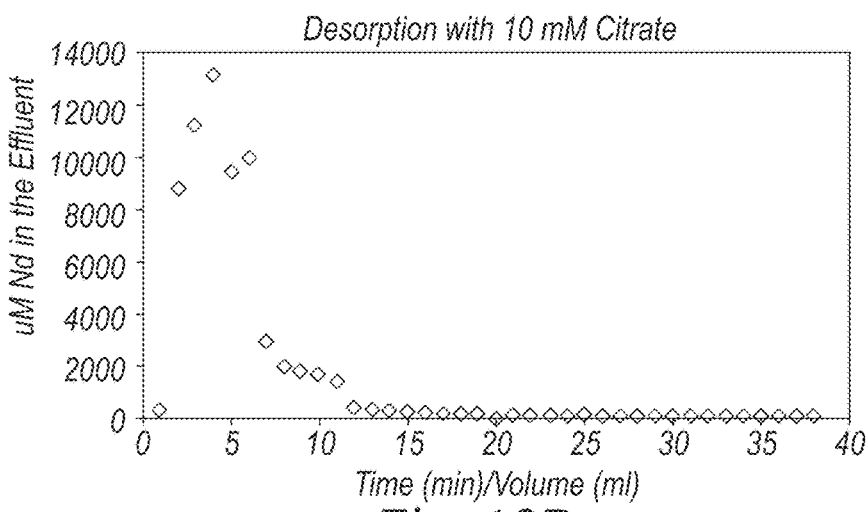
FIG. 12D is a representative plot of re-use cycles for the extraction of Nd bound to the microbes using the eluent citrate according to an embodiment of the disclosure. The plot demonstrates that using citrate as an eluent enable high efficiency desorption of Nd from the microbes, providing multiple re-use cycles.

To characterize the microbe bead resin performance and separation column parameters, a chromatography column (0.5×20 cm column) was packed with microbe beads as depicted in FIG. 12A and several breakthrough columns were run. Specifically, Nd-containing buffered solution was run through the column at various Nd concentrations and flow rates until the effluent concentration matched the influent concentration. Importantly, these results suggest that the microbe bead resin exhibited comparable REE adsorption capacity as anticipated from batch-scale experiments. The breakthrough time/volume was not affected at flow rates up 1 mL/min as shown in FIG. 12B, suggesting that adsorption kinetics is unlikely to limit the column performance. Additionally, the breakthrough time/volume was inversely proportional to the influent Nd concentration as shown in FIG. 12C. Lastly, the eluent citrate enabled high efficiency desorption of microbe bead-bound Nd, enabling multiple re-use cycles as shown in FIG. 10D.

Figure 13A:
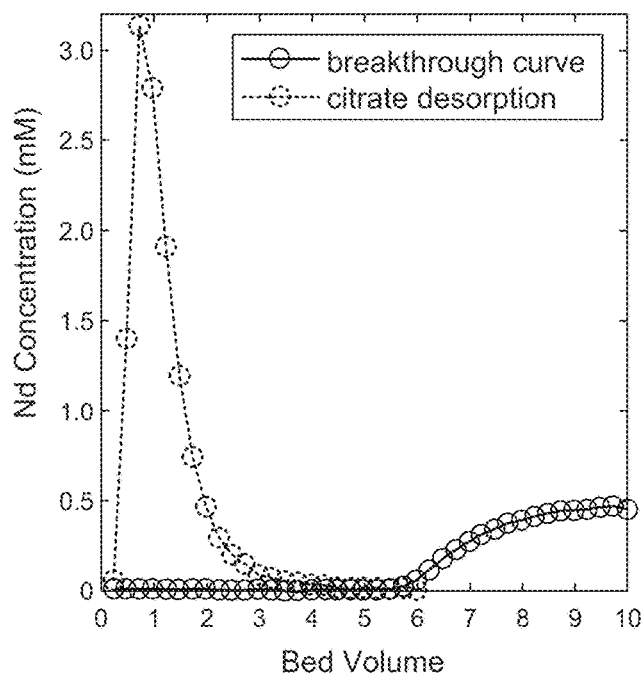
FIG. 13A is a representative plot depicting the citrate elution profile and corresponding breakthrough of Nd according to an embodiment of the present disclosure.
Figure 13B:
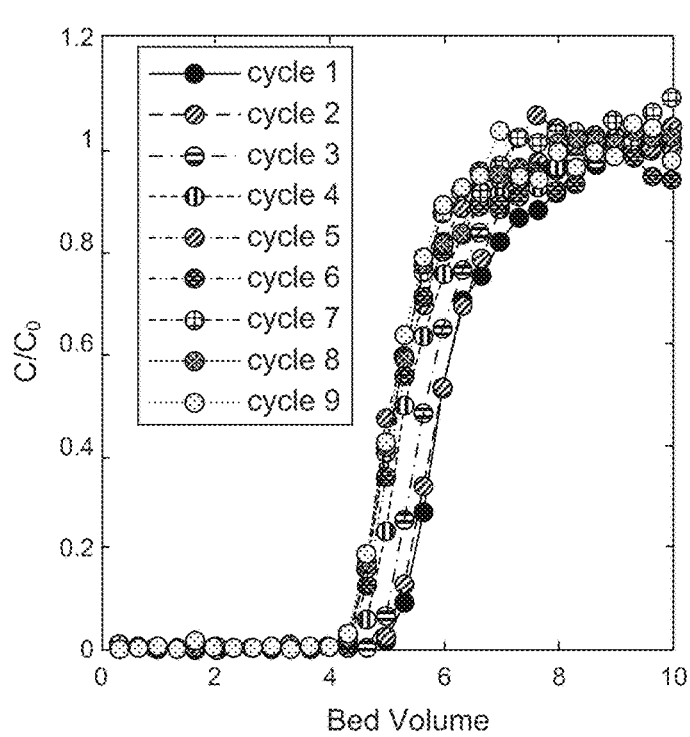
FIGS. 13B and 13C are representative breakthrough curves for nine consecutive adsorption and desorption cycles and the corresponding bead absorption capacity calculated for each cycle, respectively. These data further indicate the reusability of the beads for REE separation according to an embodiment of the present disclosure.
Figure 13C:
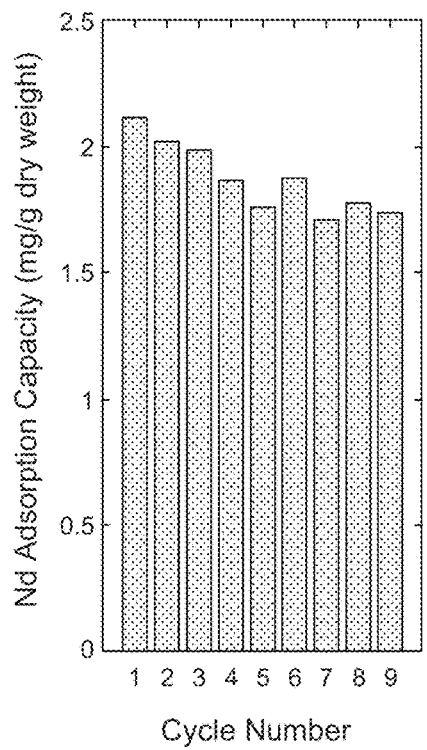

The reusability is further exemplified in FIGS. 13A-13C. In particular, FIG. 13A depicts the citrate elution profile and the corresponding breakthrough curve for the adsorption step. Further, to determine column reusability, breakthrough curves of 9 consecutive absorption and desorption cycles were collected as shown in FIG. 13B. For this experiment, an influent of 500 mM Nd in 10 mM of MES buffer at a pH of 6 was used for adsorption and 35 mL of a solution of 10 mM citrate for desorption. Between each of the adsorption and desorption cycles, the column was washed with 100 mL of 10 mM MES buffer at pH of 6. FIG. 13C further depicts the bead adsorption capacity calculated for each of the 9 cycles using mass balance from FIG. 13B. Taken together, these data indicate that the microbe bead of the present disclosure can be used through multiple reuse iterations.

In conclusion, this study demonstrates that the fine tuning of anionic eluent concentrations can facilitate the differential desorption of REEs from LBT-displayed cells. Furthermore, the REE separation system enables, not only the separation of REEs from feedstocks, but also, the separation of individual REEs, a long-standing challenge in prevailing REE separation technologies.

From the foregoing, it will be appreciated that specific embodiments of the invention have been described herein for purposes of illustration, but that various modifications may be made without deviating from the scope of the invention. Accordingly, the invention is not limited except as by the appended claims.

Para. A. A method for preferentially separating rare earth elements (REE) from a REE containing material comprising the steps of: (a) contacting genetically engineered microbes encoding at least one REE binding ligand with the REE containing material to form a microbe REE-complex; (b) introducing a tunable solution to the microbe REE-complex; and (c) separating at least a portion of the REEs from the microbe-REE complex based on affinity of the REE for the tunable solution compared to affinity of the REE for the at least one REE binding ligand, wherein at least a portion of the REEs are preferentially separated from the microbe-REE complex.

Para. B. The method of Para. A, wherein the REEs are preferentially separated from the microbe-REE complex by tuning a concentration of the tunable solution.

Para. C. The method of Para. A or Para. B, wherein step (b) further comprises introducing a tunable solution to the microbe-REE complex, wherein the REEs are simultaneously adsorbed and desorbed from the at least one REE binding ligand.

Para. D. The method of any one of Paras. A-C, further comprising repeating steps (b) and (c) by introducing a modified tunable solution to the microbe-REE complex.

Para. E. The method of Para. D, wherein the modified tunable solution has a different concentration and/or is a different tunable solution as compared to the tunable solution in step (b).

Para. F. The method of any one of Paras. A-E, further comprising repeating steps (a)-(c) with a second REE containing material.

Para. G. The method of any one of Paras. A-F, wherein steps (b) and (c) are repeated until at least about 100%, at least about 90%, at least about 80%, at least about 70%, at least about 60%, at least about 50%, at least about 40%, at least about 30%, at least about 20%, or at least about 10% of the REEs are separated from the microbe-REE complex.

Para. H. The method of any one of Paras. A-G, wherein the tunable solution is an ionic solution.

Para. I. The method of Para. H, wherein the ionic solution is an anionic solution.

Para. J. The method of Para. H, wherein the ionic solution is a cationic solution.

Para. K. The method of any one of Paras. A-K, wherein the REEs are preferentially separated from the REE containing material based on a difference in ionic radius of the REEs.

Para. L. The method of any one of Paras. A-K, wherein the REEs are preferentially separated from the REE containing material based on effects from lanthanide contractions.

Para. M. The method of any one of Paras. A-L, further comprising adding the genetically engineered microbes to a column prior to step (a).

Para. N. The method of any one of Paras. A-M, wherein the at least one REE binding ligand comprises double lanthanide binding tags (dLBTs).

Para. O. The method of Para. N, wherein the at least one REE binding ligand comprises between 2 and 12 copies of dLBTs.

Para. P. The method of any one of Paras. A-O, wherein the tunable solution has a concentration between about 0.1 mM to 1 M.

Para. Q. The method of any one of Paras. A-P, wherein the REEs are present in the REE containing material in a concentration between about 1 mM to about 1M.

Para. R. The method of any one of Paras. A-Q, wherein a concentration of the tunable solution is varied during the separating step (c).

Para. S. The method of Para. R, wherein the concentration of the tunable solution is varied by a concentration gradient to preferentially elute the REEs.

Para. T. The method of any one of Paras. A-R, wherein a pH value of the tunable solution is varied during the separating step (c).

Para. U. The method of Para. T, wherein the REE is adsorbed to the at least one REE binding ligand at a first pH value and desorbed from the at least one REE binding ligand at a second pH.

Para. V. The method of any one of Paras. A-U, wherein the concentration of the tunable solution is between about 0 mM to about 1 M, or any range there between.

Para. W. The method of any one of Paras. A-V, wherein the tunable solution comprises oxalate, an inorganic acid, an organic acid, a carbonate salt, a buffer, or any combination thereof.

Para. X. The method of Para. W., wherein the carbonate salt is a bicarbonate salt.

Para. Y. The method of Para. W, wherein the buffer is ethylenediaminetetraacetic acid (EDTA).

Para. Z. The method of any one of Paras. A-Y, wherein the separating step (c) preferentially separates individual REEs.

Para. AA. The method of any one of Paras. A-Z, wherein the separating step (c) preferentially separates groups of REEs.

Para. BB. The method of any one of Paras. A-AA, wherein the separating step (c) preferentially separates REEs adjacent to each other on a periodic table.

Para. CC. The method of any one of Paras. A-BB, wherein the separating step (c) preferentially separates Terbium (Tb), Ytterbium (Y), Lanthanum (La), or combination thereof.

Para. DD. The method of Para. CC, wherein the separating step (c) preferentially separates Tb from Neodymium (Nd), Y from Nd, La from Nd, or combination thereof.

Para. EE. The method of Para. BB, wherein REEs adjacent to each other on a periodic table are Nd and Samarium (Sm), and Homidium and Erbium (Er).

Para. FF. The method of any one of Paras. A-EE, wherein the tunable solution comprises oxalate and preferential separation of Tb from La at step (c).

Para. GG. The method of any one of Paras. A-FF, wherein the tunable solution comprises bicarbonate and preferential separation of Tb from La at step (c).

Para. HH. The method of any one of Paras. AA-GG, wherein the tunable solution comprises oxalate and preferential separation of Tb, Y, La, or combination thereof at step (c).

Para. II. The method of Para. HH, wherein the tunable solution preferentially separates Tb from Nd, Y from Nd, La from Nd, or combination thereof at step (c).

Para. JJ. The method of any one of Paras. AA-JJ, wherein the tunable solution is a 1 mM solution of oxalate and preferential separation of REEs adjacent to each other on a periodic table at step (c).

Para. KK. The method of Para. JJ, wherein the REEs adjacent to each other on the periodic table are Nd and Sm, and Ho and Er.

Para LL. The method of any one of Paras. AA-KK, wherein the tunable solution is a 2.5 mM solution of oxalate and preferential separation of REEs adjacent to each other on a periodic table at step (c).

Para. MM. The method of Para. LL, wherein the REEs adjacent to each other on the periodic table are Nd and Sm, and Ho and Er.

Para. NN. The method of any one of Paras. A-MM, wherein the concentration of the tunable solution is between about 0.1 mM to about 100 mM, or any range there between and preferential separation of dysprosium (Dy) and Nd at step (c).

Para. OO. The method of Para. NN, wherein the tunable solution comprises oxalate.

Para. PP. The method of Para. OO, wherein the tunable solution preferentially separates Dy from Tb, and Nd from Praseodymium (Pr) at step (c).

Para. QQ. The method of Para. A-PP, wherein the separating step (c) is continuous.

Para. RR. The method of Para. A-QQ, further comprising an additional step of filtration, centrifugation, or both.

Para. SS. The method of Paras. AA-RR, wherein the genetically engineered microbes are embedded into a solid support.

Para. TT. The method of Paras. AA-SS, wherein at least one REE is separated relative to any other REE, any non-REE component, and/or to any other element in a purity of at least about 10%, at least about 15%, at least about 20%, at least about 30%, at least about 40%, at least about 50%, at least about 55%, at least about 60%, at least about 65%, at least about 70%, at least about 80%, at least about 85%, at least about 90%, at least about 95%, or at least about 100%, relative to any other REE, any non-REE component, or any other element.

Para. UU. The method of any one of Paras. AA-TT, wherein a pH of the tunable solution does not change.

Para. VV. A method for preparing a bead for rare earth elements (REE) separation comprising the steps of: (a) providing genetically engineered microbes comprising an exogenous nucleic acid sequence encoding at least one REE binding ligand; and (b) emulsifying the genetically engineered microbes with at least one other component to form a high cell density bead of the genetically engineered microbes; wherein the genetically engineered microbes are embedded within or on a surface of the bead.

Para. VVW. The method of Para. VV, wherein a high cell density bead of the genetically engineered microbes has a cell density of about $10^8$ cells/mL, $10^9$ cells/mL, $10^{10}$ cells/mL, $10^{11}$ cells/mL, $10^{12}$ cells/mL, $10^{13}$ cells/mL, $10^{14}$ cells/mL, $10^{15}$ cells/mL.

Para. XX. The method of Para. VV or Para WWW, wherein the bead has an adsorption capacity of about 3 mg to about 30 mg of REE per g of the genetically engineered microbes.

Para. YY. The method of any one of Paras. VV-WWW, wherein the emulsifying step (b) enables a high cell density of the genetically engineered microbes of at least about 20 wt % or more of the total weight of the bead or at least about 20 vol % or more of the total volume of the bead.

Para. ZZ. The method of any one of Paras. VV-YY, wherein the method requires a microfluidic platform.

Para. AAA. The method of any one of Paras. VV-ZZ, wherein the emulsifying step (b) comprises mixing the genetically engineered microbes and at least one other component.

Para. BBB. The method of any one of Paras. VV-AAA, wherein the at least one other component is a polymer, a photoinitiator, an oil, or any combination thereof.

Para. CCC. The method of any one of Paras. VV-BBB, further comprising a polymerization step after emulsifying the genetically engineered microbes with at least one other component.

Para. DDD. The method of any one of Paras. VV-CCC, further comprising incorporating the bead into a column, membrane, bead, or combination thereof.

Para. EEE. A kit of parts comprising: (a) genetically engineered microbes comprising an exogenous nucleic acid sequence encoding at least one REE binding ligand; (b) a tunable solution; and (c) instructions for differentially separating REEs from a REE containing material.

Para. FFF. The kit of parts of Para. EEE, wherein the tunable solution is an ionic solution.

Para. GGG. The kit of parts of Para. EEE or Para. FFF, wherein the tunable solution is an anionic solution.

Para. HHH. The kit of parts of any one of Paras. EEE-GGG, wherein the tunable solution is a cationic solution.

Para. III. The kit of parts of any one of Paras. EEE-HHH, wherein the tunable solution comprises oxalate, an inorganic acid, an organic acid, a carbonate salt, a buffer, or any combination thereof.

Para. JJJ. The kit of parts of any one of Paras. EEE-III, wherein the at least one REE binding ligand comprises double lanthanide binding tags (dLBTs).

Para. KKK. The kit of parts of Para. JJJ, wherein the at least one REE binding ligand comprises between 2 and 12 copies of dLBTs.

Para. LLL. A bead for rare earth elements (REE) separation comprising genetically engineered microbes comprising an exogenous nucleic acid sequence encoding at least one REE binding ligand emulsified with at least one other component, wherein the bead has a high cell density of the genetically engineered microbes.

Para. MMM. The bead of Para. LLL, wherein the high cell density of the genetically engineered microbes is at least about 20 wt % or more of the total weight of the bead or at least about 20 vol % or more of the total volume of the bead.

Para. NNN. The bead of Para. LLL or Para. MMM, wherein the at least one other component is a polymer, a photoinitiator, an oil, or any combination thereof.

Para. OOO. The bead of any one of Paras. LLL-NNN, wherein the genetically engineered microbes are embedded within or on a surface of the bead.

Para. PPP. The bead of any one of Paras. LLL-OOO, wherein the at least one REE binding ligand comprises double lanthanide binding tags (dLBTs).

Para. QQQ. The bead of Para. PPP, wherein the at least one REE binding ligand comprises between 2 and 12 copies of dLBTs.

Para RRR. The method of any one of Para. A-E, wherein the microbe-REE complex is formed in step (a) at a temperature between about 23° C. to about 100° C.

Para. SSS. The method of Para. D, wherein a temperature of the modified tunable solution is different than the temperature in step (a).

We claim:

1. A method for preferentially separating an individual rare earth element (REE) from an REE containing material, the method comprising the steps of:
    a) contacting genetically engineered microbes encoding at least one REE binding ligand with the REE containing material to form a microbe REE-complex;
    b) introducing a tunable solution to the microbe REE-complex; and
    c) separating the individual REE from the microbe-REE complex based on affinity of the individual REE for the tunable solution compared to affinity of the REE for the at least one REE binding ligand, wherein
    the REE containing material includes a plurality of different REEs and the individual REE is separated from the plurality of different REEs.

2. The method of claim 1, wherein the individual REE is preferentially separated from the microbe-REE complex by tuning a concentration of the tunable solution.

3. The method of claim 1, wherein step (b) further comprises introducing a tunable solution to the microbe-REE complex, wherein the REEs are simultaneously adsorbed and desorbed from the at least one REE binding ligand.

4. The method of claim 1, further comprising repeating steps (b) and (c) by introducing a modified tunable solution to the microbe-REE complex.

5. The method of claim 4, wherein the modified tunable solution has a different concentration and/or is a different tunable solution as compared to the tunable solution in step (b).

6. The method of claim 1, wherein the microbe-REE complex is formed in step (a) at a temperature between 23° C. to 100° C.

7. The method of claim 4, wherein a temperature of the modified tunable solution is different than the temperature in step (a).

8. The method of claim 1, wherein the at least one REE binding ligand comprises double lanthanide binding tags (dLBTs).

9. The method of claim 8, wherein the at least one REE binding ligand comprises between 2 and 12 copies of dLBTs.

10. The method of claim 1, wherein a concentration of the tunable solution is varied during the separating step (c).

11. The method of claim 1, wherein the tunable solution comprises oxalate, an inorganic acid, an organic acid, a carbonate salt, a buffer, or any combination thereof.

12. The method of claim 1, wherein the REE containing material is:
    a low grade material, wherein the REEs are present in less than 2 wt % of a total weight of the low grade material; or
    a high grade material wherein the REEs are present in an amount greater than 2 wt % of a total weight of the high grade material.

13. The method of claim 1, wherein the individual REE is separated relative to any other REE, any non-REE component, and/or to any other element in a purity of at least 10%, at least 15%, at least 20%, at least 30%, at least 40%, at least 50%, at least 55%, at least 60%, at least 65%, at least 70%, at least 80%, at least 85%, at least 90%, at least 95%, or at least 100%.

14. A bead for rare earth elements (REE) separation comprising genetically engineered microbes comprising an exogenous nucleic acid sequence encoding at least one REE binding ligand emulsified with at least one other component, wherein the bead has a high cell density of the genetically engineered microbes of at least 20 wt % or more of a total weight of the bead or least 20 vol % or more of a total volume of the bead, and
    the bead is configured to preferentially separate an individual REE from an REE containing material, wherein the REE containing material includes a plurality of different REEs and the individual REE is separated from the plurality of different REEs, by:
        contacting the bead with the REE containing material to form a microbe REE-complex; and after an introduction of a tunable solution to the microbe REE-complex, separating the individual REE from the microbe-REE complex based on an affinity of the individual REE for the tunable solution compared to affinity of the REE for the at least one REE binding ligand.

15. The bead of claim 14, wherein the at least one REE binding ligand comprises double lanthanide binding tags (dLBTs).

16. A method for preferentially separating a group of rare earth elements (REEs) from an REE containing material, the method comprising the steps of:
a) contacting genetically engineered microbes encoding at least one REE binding ligand with the REE containing material to form a microbe REE-complex;
b) introducing a tunable solution to the microbe REE-complex; and
c) separating the group of REEs from the microbe-REE complex based on affinity of the group of REEs for the tunable solution compared to affinity of group of REEs for the at least one REE binding ligand
the REE containing material includes a plurality of different REEs and the group of REEs is separated from the plurality of different REEs.

17. The method of claim 16, wherein the group of REEs are heavy REEs selected from one or more of Gd, Tb, Dy, Ho, Er, Tm, Yb, Lu, Sm, or Y.

18. The method of claim 16, wherein the group of REEs are light REEs selected from one or more La, Cr, Pr, Nd, Sm, or Eu.

19. The method of claim 16, wherein the group of REEs are preferentially separated from the microbe-REE complex by tuning a concentration of the tunable solution.

20. The method of claim 16, wherein step (b) further comprises introducing a tunable solution to the microbe-REE complex, wherein the REEs are simultaneously adsorbed and desorbed from the at least one REE binding ligand.

21. The method of claim 16, further comprising repeating steps (b) and (c) by introducing a modified tunable solution to the microbe-REE complex.

22. The method of claim 16, wherein the at least one REE binding ligand comprises double lanthanide binding tags (dLBTs).

23. The method of claim 22, wherein the at least one REE binding ligand comprises between 2 and 12 copies of dLBTs.

24. A method for preferentially separating rare earth elements (REEs) adjacent to each other on a periodic table from an REE containing material, the method comprising the steps of:
a) contacting genetically engineered microbes encoding at least one REE binding ligand with the REE containing material to form a microbe REE-complex;
b) introducing a tunable solution to the microbe REE-complex; and
c) separating an REE adjacent to another REE on the periodic table from the microbe-REE complex based on affinity of the REE for the tunable solution compared to affinity of the REE for the at least one REE binding ligand, wherein:
the REE containing material includes at least the REE and another REE adjacent to the REE on the periodic table.

25. The method of claim 24, comprising separating La from Ce, Ce from Pr, Pr from Nd, Nd from Pm, Pm from Sm, Sm from Eu, Eu from Gd, Gd from Tb, Tb from Dy, Dy from Ho, Ho from Er, Er from Tm, Tm from Yb, and/or Yb from Lu.

26. The method of claim 24, wherein the REEs adjacent to each other on the periodic table are preferentially separated from the microbe-REE complex by tuning a concentration of the tunable solution.

27. The method of claim 24, wherein step (b) further comprises introducing a tunable solution to the microbe-REE complex, wherein the REEs are simultaneously adsorbed and desorbed from the at least one REE binding ligand.

28. The method of claim 24, further comprising repeating steps (b) and (c) by introducing a modified tunable solution to the microbe-REE complex.

29. The method of claim 24, wherein the at least one REE binding ligand comprises double lanthanide binding tags (dLBTs).

30. The method of claim 29, wherein the at least one REE binding ligand comprises between 2 and 12 copies of dLBTs.

* * * * *